United States Patent
German et al.

(10) Patent No.: US 6,258,789 B1
(45) Date of Patent: *Jul. 10, 2001

(54) DELIVERY OF GENE PRODUCTS BY INTESTINAL CELL EXPRESSION

(75) Inventors: Michael German, San Francisco; Ira D. Goldfine, Kentfield; Stephen S. Rothman, Berkeley, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/254,988

(22) PCT Filed: Sep. 18, 1997

(86) PCT No.: PCT/US97/16523
    § 371 Date: Jun. 11, 1999
    § 102(e) Date: Jun. 11, 1999

(87) PCT Pub. No.: WO98/11779
    PCT Pub. Date: Mar. 26, 1998

Related U.S. Application Data

(63) Continuation-in-part of application No. 08/717,084, filed on Sep. 20, 1996.

(51) Int. Cl.$^7$ .................................................. A61K 48/00

(52) U.S. Cl. .................... 514/44; 435/320.1; 435/455; 435/458

(58) Field of Search ................. 514/44; 424/93.2, 424/93.21; 435/320.1, 455, 458, 325, 69.1

(56) References Cited

U.S. PATENT DOCUMENTS

| | | | |
|---|---|---|---|
| 5,292,662 | 3/1994 | Sandmeyer | 435/320.1 |
| 5,328,470 | * 7/1994 | Nabel et al. | 604/101 |
| 5,643,579 | * 7/1997 | Hung et al. | 424/227.1 |
| 5,681,744 | 10/1997 | Greenstein | 435/320.1 |
| 5,786,340 | 7/1998 | Henning et al. | 514/44 |
| 5,821,235 | 10/1998 | Henning et al. | 514/44 |
| 5,874,415 | * 2/1999 | Kufe et al. | 514/44 |

FOREIGN PATENT DOCUMENTS

| | | |
|---|---|---|
| WO 90/11092 | 10/1990 | (WO) . |
| WO 93/03769 | 3/1993 | (WO) . |
| WO 93/19660 | 10/1993 | (WO) . |
| WO 94/25608 | 11/1994 | (WO) . |
| WO 96/40081 | 12/1996 | (WO) . |

OTHER PUBLICATIONS

Batra, 1994. "Molecular Conjugate Vectors Mediate Efficient Gene Transfer into Gastrointestinal Epithelial Cells," *Cancer Gene Therapy* 1(3):185–92.

Benvenisty, et al., 1986. "Direct Introduction of Genes Into Rats and Expression of the Genes," *Proc. Nat'l. Acad. Sci. USA* 83:9551–5.

Chang, et al., 1994. "Gene Therapy: Applications to the Treatment of Gastrointestinal and Liver Diseases," *Gastroenterol.* 106:1076–84.

Coghlan, 1995. "Gene Dream Fades Away," *New Scientist* 148:14–15.

Docherty, 1997. "Gene Therapy for Diabetes Mellitus," *Clinical Science* 92:321–330.

Dubensky, et al. 1984. "Direct Transfection of Viral and Plasmid DNA into the Liver of Spleen of Mice," *Proc. Nat'l. Acad. Sci. USA* 81:7529–7533.

German, et al., 1994. "The Insulin Gene Contains Multiple Transcriptional Elements that Respond to Glucose," *Mol. Cell Biol.* 14:4067.

Jones, et al., 1990. "Ectopic Correction of Ornithine Transcarbamylase Deficiency in Sparse Fur Mice," *J. Biol. Chem.* 264(24):14684–90.

Lau, et al, 1992. "The Intestine as a Possible Site for Gene Therapy," *J. Cell Biochem.* 16F(V215):48.

Ledley, 1992. "Somatic Gene Therapy in Gastroenterology: Approaches and Applications," *J. Pediatr. Gastroenterol. Nutr.* 14:328–37.

Ledley, "Nonviral Gene Therapy: The Promise of Genes as Pharmaceutical Products," *Human Gene Therapy* (Sep. 1995) 6:1129–1144.

Liebow, et al., 1975. "Enteropancreatic Circulation of Digestive Enzymes," *Science* 189:472–474.

Mastrangelo, et al., 1996. "Gene Therapy for Human Cancer: An Essay for Clinicians," *Seminars in Oncology* 23(1):4–21.

Maziere, et al., 1992. "Processing and Characterization of the Low Density Lipoprotein Receptor in the Human Colonic Carcinoma Cell Subclone HT29–18: A Potential Pathway for Delivering Therapeutic Drugs and Genes," *Bioscience Reports* 12(6)483–94.

Morsey, et al., 1993. "Progress Toward Human Gene Therapy," *JAMA* 270(19):2338–2345.

Noel, et al., 1994. "Optimization of Gene Transfer into Intestinal Epithelial Cells Using a Retroviral Vector," *J. Ped. Gastroenterol. Nutr.* 19(1):43–9.

Puppi, et al., 1995. "Cloning of the Rat Ecotropic Retroviral Receptor and Studies of Its Expression in Intestinal Tissues," *P.S.E.B.M.* 209:38–45.

Rosenfeld, et al., 1991. "Adenovirus–Mediated Transfer of a Recombinant α1–Antitrypsin Gene to the Lung Epithelium in Vivo," *Science* 252:431–4.

(List continued on next page.)

*Primary Examiner*—Dave Nguyen
(74) *Attorney, Agent, or Firm*—Carol L. Francis; Paula A. Borden; Bozicevic, Field & Francis LLP

(57) ABSTRACT

Intestinal epithelial cells of a mammalian subject are genetically altered to operatively incorporate a gene which expresses a protein which has a desired effect. The method of the invention comprises administration of a formulation containing DNA to the gastrointestinal tract, preferably by an oral route. The expressed recombinant protein is secreted directly into the bloodstream. Of particular interest is the use of the method of the invention to provide for short term delivery of gene products to the bloodstream.

5 Claims, 10 Drawing Sheets

OTHER PUBLICATIONS

Sanberg, et al., 1994. "Improving Access to Intestinal Stem Cells as a Step Toward Intestinal Gene Transfer," *Hum. Gene Therapy* 5:303–9.

Soriano–Bucher, et al, 1991. "Gene Transfer into the Intestinal Epithelium," *Gastroenterol.* 100(5):A252.

Sweester, et al., 1988. "Transgenic Mice Containing Intestinal Fatty Acid–Binding Protein–Human Growth Hormone Fusion Genes Exhibit Correct Regional and Cell–Specific Expression of the Reporter Gene in their Small Intestine," *Proc. Nat'l. Acad. Sci. USA* 85:9611–5.

Takehara, et al., 1996. "In Vivo Gene Transfer and Expression in Rat Stomach by Submucosal Injection of Plasmid DNA," *Human Gene Therapy* 7:589–593.

Taneguchi, et al. 1997. "Constant Delivery of Proinsulin by Encapsulation of Transfected Cells," *J. of Surgical Res.* 70:41–45.

Traber, et al., 1992. "Novel DNA–Binding Proteins Regulate Intestine–Specific Transcription of the Surase–Isomaltase Gene," *Mol. Cell Biol.* 12(8)3614–27.

Crystal, 1995. "Transfer of genes to humans: early lessons and obstacles to success ," *Science* 270:404–410.

Coghlan, New Scientist, vol. 148, pp. 14 and 15, 1995.*

Anderson, Nature, vol. 392, 25–30, Apr. 1998.*

Gunzburg et al., vol. 1, No. 9, pp. 410–417, 1995.*

Wirtz et al. (GUT, 44, 6, pp. 800–807), 1999.*

Cryz et al., Vaccine, vol. 14, 7, Vaccine Delivery Systems, Reports of the Expert Panels, pp. 665–688, 1996.*

Doerfler et al. (Gene, 157/1–2, pp. 241–245), 1995.*

Filion et al. (Int. J. Pharm., 162(1–2), pp. 159–170), 1998.*

Tait et al. (Clinical Cancer Res., vol. 5, 1707–1714), 1999.*

Takehara et al. (Human Gene Therapy, vol. 7, pp. 589–593), Mar. 1996.*

Westbrook et al. (Human Molecular Genetics, vol. 3, 11, pp. 2005–2010), 1994.*

Weidenbach et al. (Zeitschrift Fur Gastroenterologie, 32, 12, pp. 665–70), 1994.*

* cited by examiner

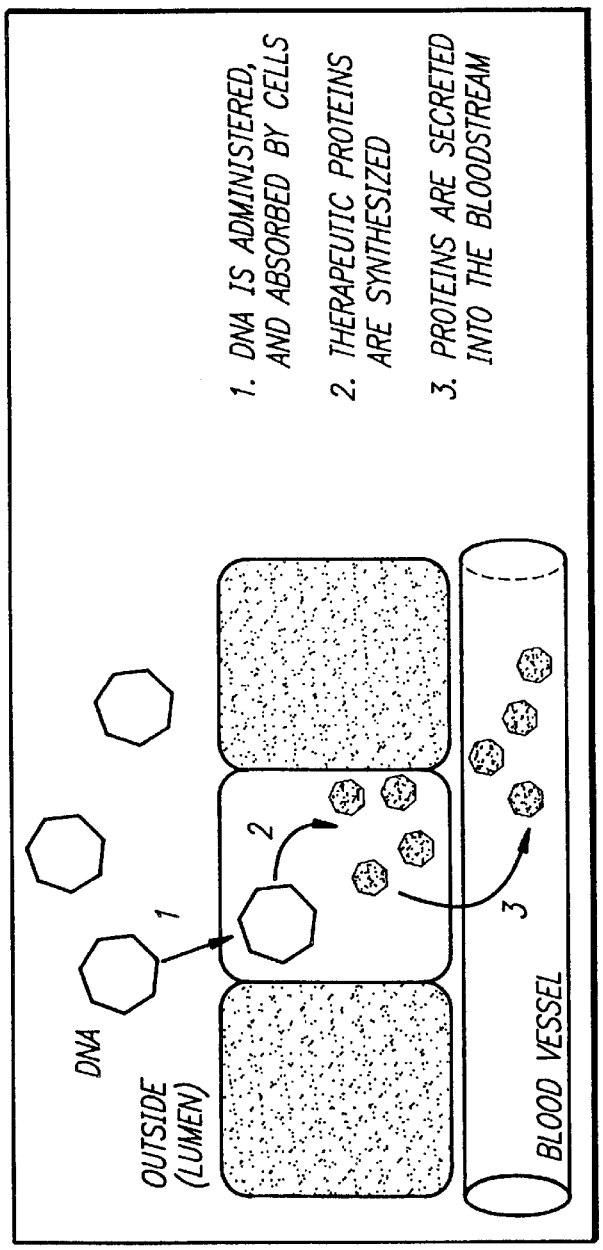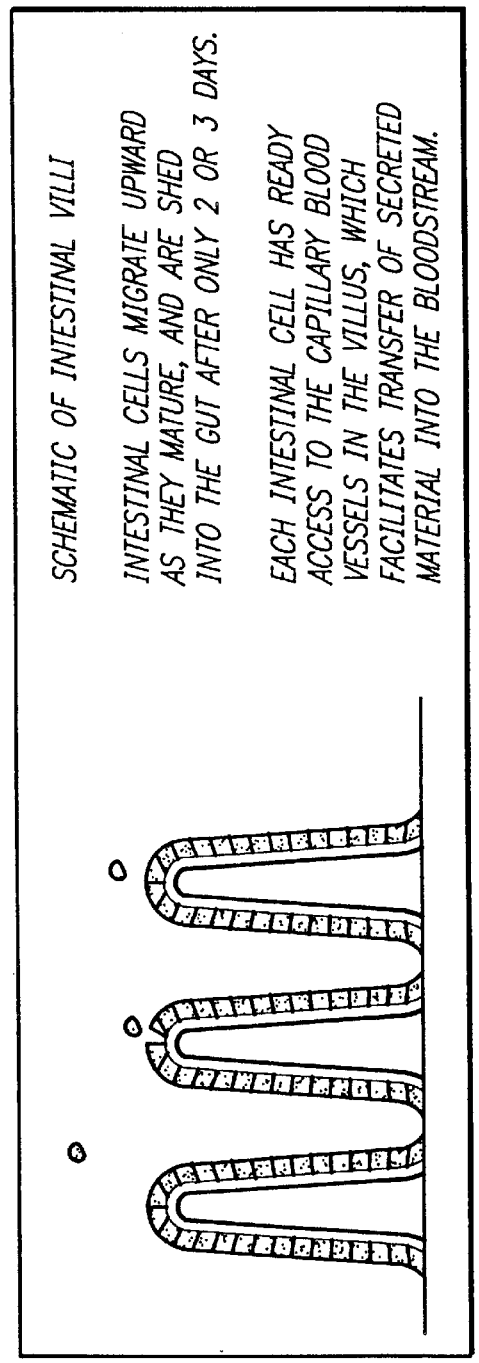

DELIVERY OF GENE PRODUCTS BY INTESTINAL CELL EXPRESSION

This application is a continuation-in-part of U.S. application Ser. No.08/717,084, filed Sep. 20, 1996, which application is hereby incorporated by reference.

FIELD OF THE INVENTION

This invention relates generally to the field of drug delivery, more particularly to the delivery of therapeutic gene products by transformation of cells of the intestine.

BACKGROUND OF THE INVENTION

Proteins are essential to all biological functions, from metabolism, to growth, to reproduction, to immunity. As such, they have an important potential role as pharmaceutical agents for the treatment of a wide range of human diseases. Indeed, they have already been used to treat diseases such as cancer, hemophilia, anemia and diabetes successfully, and for a number of diseases are the only effective treatment.

Although protein drugs have enormous therapeutic potential, their more widespread use has been limited by several restrictive technical factors. First, proteins remain difficult and expensive to manufacture compared to other pharmaceuticals. Large-scale purification of proteins in bioactive form can be a limiting step in the commercialization of these drug. Second, many proteins are metabolized or otherwise eliminated quickly in the patient. This results in the need for frequent re-administration. Finally, protein drugs generally must be given by injection. This increases the complexity and expense of the treatment, and the disagreeable nature of administration also limits potential clinical applications.

Delivery of therapeutic gene products (such as polypeptides for protein replacement therapy) by expression in cells transformed with a therapeutic gene product-encoding DNA has attracted wide attention as a method to treat various mammalian diseases and enhance production of specific proteins or other cellular products. This promising technology, often referred to as gene therapy, is generally accomplished by introducing exogenous genetic material into a mammalian patient's cells. The introduced genetic material can be designed to replace an abnormal (defective) gene of the mammalian patient ("gene replacement therapy"), or can be designed for expression of the encoded protein or other therapeutic product without replacement of any defective gene ("gene augmentation"). Because many congenital and acquired medical disorders result from inadequate production of various gene products, gene therapy provides a means to treat these diseases through either transient or stable expression of exogenous nucleic acid encoding the therapeutic product.

Delivery of therapeutic gene products by expression in transformed cells can be accomplished by either direct transformation of target cells within the mammalian subject (in vivo gene therapy) or transformation of cells in vitro and subsequent implantation of the transformed cells into the mammalian subject (ex vivo gene therapy). A variety of methods have been developed to accomplish in vivo transformation including mechanical means (e.g., direct injection of nucleic acid into target cells or particle bombardment), recombinant viruses, liposomes, and receptor-mediated endocytosis (RME) (for reviews, see Chang et al. 1994 *Gastroenterol.* 106: 1076–84; Morsey et al. 1993 *JAMA* 270: 2338–45; and Ledley 1992 *J. Pediatr. Gastroenterol. Nutr.* 14: 328–37).

As with all therapies, the therapy that is most easily administered, least expensive, and most likely to realize patient compliance is the therapy of choice. Intestinal gene therapy provides such a therapy in the realm of gene therapy techniques. The intestinal epithelium is a particularly attractive site for in vivo gene therapy, largely due to the ease of access via an oral or other lumenal route, thus allowing administration of the exogenous nucleic acid via non-invasive procedures. For example, the patient can simply take a pill composed of the exogenous nucleic acid or alternatively the exogenous nucleic acid formation can be administered by some other non-invasive means (i.e., a means that does not require a major surgical procedure, such as endoscopic catheterization or rectal suppository incision).

However, past efforts to accomplish in vivo transformation of intestinal cells have met with severe obstacles. Because the field has been primarily concerned with long-term transformation and delivery of the therapeutic gene product of interest, most groups have shunned intestinal epithelial cells as targets for transformation due to the cells' rapid turn-over rate (2 to 4 days) (see, e.g., Sandberg et al. 1994 *Hum. Gene Therap.* 5: 303–9). Efforts to achieve in vivo transformation may be further complicated by the mucus layer of the intestine, which is thought to block access of the gene therapy transforming formulation to the target cells (Sandberg et al., supra). The presence of high concentrations of DNAses in the intestinal tract is also thought to be a formidable barrier to the effective introduction of DNA into intestinal tract cells.

Many of the vectors and delivery systems developed for in vivo cellular transformation either have their own inherent drawbacks or are not entirely suitable for in vivo intestinal cell transformations. For example, recombinant viruses, particularly retroviruses, may be slow in gaining FDA approval due to concerns generally associated with the administration of live viruses to humans. In addition, it has become clear that viral vectors present problems with the possibility of multiple administrations of the gene construct due to immune responses, and may greatly limit their utility. Mechanical means, such as the gene gun, are designed for use in transformation of skeletal muscle cells and are not particularly useful in intestinal cell transformation due to problems of access and to the delicate nature of organ.

Current methods for drug delivery by transformation that are designed to accomplish systemic therapeutic goals (e.g., to accomplish administration of protein-based drugs) include both ex vivo and in vivo techniques. However ex vivo techniques require complex procedures to accomplish transformation, put the subject at risk of rejection of the transplant, require at least minor invasive procedures, and limit implantation to modest numbers of cells. In vivo methods (e.g., direct administration through blood or to muscle) also frequently require invasive procedures and meet with difficulties in delivery of the transforming material to the target cell. Moreover, delivery of the transforming material via the bloodstream of the individual results in exposure of the DNA and any carrier associated with it to the immune system, which can result in adverse reactions (e.g., inflammatory reactions to the DNA administered and/or to components of the formulation containing the DNA.

Today, as the biomedical research enterprise discovers new proteins at an increasing pace, and as known proteins become available as therapeutic agents, there is a vital need to develop new delivery systems and methods to expand the application of these molecules as drugs by improving the feasibility and convenience of their use. The present invention addresses these problems.

SUMMARY OF THE INVENTION

Intestinal epithelial cells are genetically altered by exposure to a formulation comprising nucleic acids (including DNA, RNA, DNA-RNA hybrids, oligonucleotides, and synthetic nucleic acids), where such exposure results in the nucleic acid being operatively incorporated into the intestinal epithelial cell, thereby facilitating expression of a gene encoding a therapeutically effective protein. The nucleic acid formulation can be any formulation suitable for delivery to the gastrointestinal tract for introduction of the nucleic acid in the formulation into an intestinal epithelial cell including viral vectors, naked nucleic acid, and/or liposome formulation, preferably naked nucleic acid. More particularly, cells of the intestine are genetically altered to operatively incorporate a functional exogenous DNA sequence which, when expressed, produces a protein that is secreted directly from the cell into the bloodstream and/or into the gastrointestinal system in an amount sufficient to obtain therapeutic levels of the protein, thereby treating the patient in need of the protein. The method of the invention can thus be used to genetically alter cells to accomplish systemic therapy and/or repair of defects in the transfected cell itself.

A primary object is to provide a method of therapeutic gene product (e.g., protein) delivery wherein cells of the intestinal epithelium (e.g., cells of the small intestine or the large intestine) of a mammal are genetically modified by the incorporation of full functional genes (exogenous DNA) which express a biologically active and therapeutically useful protein, which protein is secreted from the modified cells into the circulatory system, the gastrointestinal tract, and/or the local environment of gastrointestinal tissue.

Another object is to produce genetically transformed intestinal epithelial cells which have incorporated into their genome exogenous genetic material in the form of a fully functional gene which expresses a biologically active and therapeutically useful protein that functions within the cell. Alternatively, the transfected nucleic acid can provide structural, enzymatic or other direct intracellular effects independent of coding for a gene product. Examples include anti-sense nucleic acids that effect the regulation and expression of endogenous genes, and ribozymes which are nucleic acid sequences having intrinsic enzymatic activity.

The present invention is advantageous in that it exploits the enormous ability of cells lining the GI tract to produce and secrete proteins. The intestines are the second largest organ of the body, and largest immune organ. The cells of the intestinal wall provide an interface with tremendous surface area (approx. 300 $m^2$) that has as its normal function the preferential absorption of substances from the GI tract and transfer into the bloodstream; this is not the case for lung or muscle tissues. Making use of even a small fraction of this capacity can provide many important therapeutic proteins, such as hormones, cytokines, and clotting protein, to the bloodstream. Moreover, short-acting proteins can be used with greater therapeutic effect as the present invention ensures their continuous synthesis and secretion at the needed rates.

An important advantage of the present invention is that it allows administration of protein drugs by mouth. Rather than attempting to deliver the protein itself, the delivery system of the invention does so indirectly by administering the gene encoding the therapeutic proteins. Despite the conventional wisdom that any DNA in the gastrointestinal tract would be destroyed rapidly by the digestive process (either by stomach acid or intestinal DNAse), oral delivery of DNA encoding a desired therapeutic protein is successful in the present invention. The DNA is taken up by intestinal cells, which synthesize the encoded protein and secrete it into the bloodstream or the gastrointestinal tract to achieve therapeutic results. The flexibility of this technology allows for the delivery of a wide variety of protein pharmaceuticals, systemically, into the gastrointestinal tract, as well as locally, making it well suited for a broad spectrum of therapeutic applications.

Another advantage of the present invention is that the short term expression of the therapeutic gene in the individual allows for regulation of administration of the therapeutic gene product to the patient. Because intestinal cells turn over rapidly, expression can be easily modified or altered by varying the dose and/or formulation of the oral preparation. Short-term expression is thus a consequence of the rapid turnover of transformed cells that are normally lost (or "turned over") within about two or three days. This aspect of the invention is both advantageous for dose control and reduction of risk of long-term complications from DNA integration (mutagenesis).

Another advantage of the invention is that the method completely avoids invasive procedures, and allows the vector to be administered in the simplest possible fashion—by the oral administration of a pill or other material. The lumen of the gastrointestinal tract is actually "outside" the body, and is separated from it by a single continuous layer of cells. As such, anything that passes into the gastrointestinal tract through the mouth remains in the exterior space, and cannot enter the body proper and its bloodstream, unless it first crosses the cells that line the gastrointestinal tract. However, once the gene is expressed within the intestinal cells and the protein product released into the bloodstream via natural secretory pathways, the therapeutic protein acts in the same manner as current, injectable forms of the drug.

The present invention is also advantageous over gene-based therapies that administer the gene vector into the bloodstream to other tissues and organs in that is involves administration of the DNA of interest directly to the target cells of the subject without first being distributed broadly via the bloodstream. Thus delivery of the DNA using the invention is more efficient and avoids the need for additional mechanisms to target the DNA of interest to a particular tissue.

Still another advantage is that the present invention minimizes the exposure of the transforming DNA to the bloodstream, the major source of adverse reactions to treatment. Reaction by the immune system to the delivery vector (particularly viral vectors) is a major obstacle for conventional gene-based therapies. Delivery of vectors by other routes (e.g., intravenous, intramuscular injection, or plumonary administration exposes them to blood and extracelluar fluid. This exposure commonly results in inflammation and an immune response. These adverse reactions often worsen with reapplication, to the point where treatment cannot continue and becomes completely ineffective. The present invention presents the vector directly to the intestines without having to pass first through the blood or tissue of the subject. This shield the DNA delivery process as much as possible from the systemic circulation where immunological and inflammatory responses are initiated, and in this way minimizes their interference with therapy.

Another advantage of the invention is that naked DNA can be used as the vector, rather than viral vectors. Although viral vectors have been popular for gene therapy due to ease of administration and the incorporation of DNA into the genome, viral vectors have been found to produce substantial antigenic reactions that prevent their multiple administration. Use of naked DNA avoids this problem.

Yet another advantage of the invention is that potential deleterious side-effects of long term gene administration can be avoided, because the epithelial cells are sloughed into the intestinal lumen and lost from the body within a few days.

Another advantage of the invention is that the therapeutic gene product is delivered to the bloodstream of the subject in a manner and dosage that is more akin to normal production of the gene product (e.g., relative to bolus intravenous injection of a therapeutic polypeptide).

Still yet another advantage is that the drug delivery system of the invention uses the patient's own tissue to produce the protein drug of interest and secrete it into the bloodstream.

Another advantage of the invention is that administration of DNA formulations directly to the lumen of the GI tract (rather than to the bloodstream) allows for the use of a greater variety of transfection adjuvants. As a result of its physiological role, the gastrointestinal tract is designed to be more robust, and is more able to tolerate a wider range of environmental conditions and less susceptible to toxic reactions. Thus the present invention can be used in conjunction with chemical methods to facilitate DNA uptake by cells that are suitable alternative to viral-based vectors, but may be otherwise unsuitable to administration via intravenous, intramuscular, or pulmonary routes. For example, since the GI tract is less susceptible to toxicity and does not require targeting from the circulation, the present invention allows expanded use of liposomes, adjuvants that are comprised of cationic lipids and enhance DNA uptake, as well as a variety to other adjuvants.

The invention is also advantageous in that it avoids many of the technical barriers associated with delivery of protein-based drugs. First, the invention avoids the cost and difficulty of manufacture of proteins by using the body's own tissues to synthesize the desired proteins. Second, the invention avoids the problems of rapid metabolism by providing for the continuous manufacture and secretion of the therapeutic protein by gene expression. Finally, oral administration avoids the need for injection to achieve therapeutic levels in the body.

These and other objects, advantages and features of the present invention will become apparent to those persons skilled in the art upon reading the details of the vectors, formulations, methodology as more fully set forth below.

BRIEF DESCRIPTION OF THE DRAWINGS

FIG. 1 is a schematic of the epithelial cell layer lining the gastrointestinal tract. Step 1 represents administration of DNA and absorption by cells in the intestinal tract; step 2 represents synthesis of therapeutic proteins; and step 3 represents secretion of proteins into the bloodstream.

FIG. 2 is a schematic of intestinal villi showing the sloughing of intestinal cells from the tip of the villus after their migration from the stem cells at the villus base.

DESCRIPTION OF THE PREFERRED EMBODIMENTS

Figure 3:
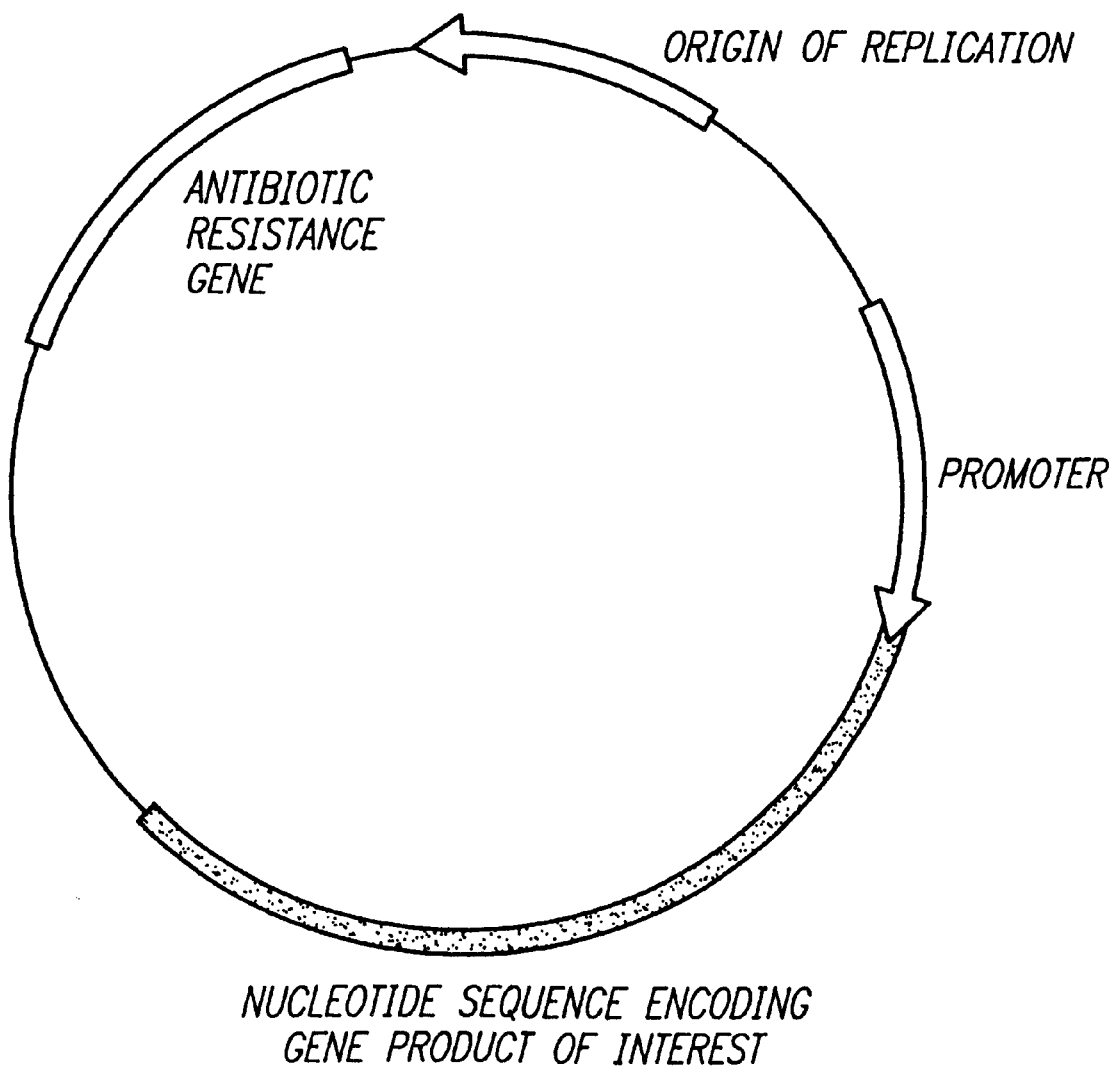
FIG. 3 is a schematic view of an exemplary recombinant plasmid construct useful in transformation of intestinal epithelial cells according to the invention.

Before the present method of genetically transforming intestinal epithelial cells and methods for providing gene therapy are described, it is to be understood that this invention is not limited to the particular methodology, protocols, cell lines, intestinal cells, vectors and reagents described and as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a" and "the" include plural referents unless the context clearly dictates otherwise. Thus, for example, reference to "an intestinal epithelial cell" includes a plurality of such cells and reference to "the transformation vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

Definitions

By "intestine" is meant the lower part of the alimentary canal, which extends from the stomach to the anus and is composed of a convoluted upper part (small intestine) and a lower part of greater diameter (large intestine).

By "small intestine" is meant the region of the intestine composed of the duodenum, jejunum, and ileum.

By "large intestine" is meant the region of the intestine composed of the ascending colon, transverse colon, descending colon, sigmoid colon, and rectum.

By "intestinal epithelial cell" is meant a cell contained within the tissues that cover the lumenal surface of the intestine, including, but not necessarily limited to, absorptive cells of the small intestine, columnar epithelial cells of the large intestine, endocrine cells (large and small intestine), and crypt cells (including mucous gland cells, serous gland cells, and stem cells). Of particular interest are "short-lived" epithelial cells, i.e., cells that are shed into the gastrointestinal lumen within about two or three days after maturation (as opposed to "long-lived" epithelial cells such as the stem cells.

By "transformation" is meant a transient (i.e., episomal or otherwise non-inheritable) or permanent (i.e., stable or inheritable) genetic change induced in a cell following incorporation of new DNA (i.e., DNA exogenous to the cell).

By "naked DNA" or "naked nucleic acid" or DNA sequence and the like is meant a nucleic acid molecule that is not contained within a viral particle. Naked nucleic acid can be associated with non-viral means for facilitating delivery of the nucleic acid to the site of the target cell (e.g., means that facilitate travel of the nucleic acid through the alimentary canal, protect the nucleic acid from stomach acid, serve to penetrate intestinal mucus to the surface of the target epithelial cell, and/or penetrate the cell membrane) and/or viral or non-viral components that act as adjuvants (e.g., viral particles that are administered in conjunction with the naked DNA, but do not contain the DNA to be delivered to the target cells).

By "transformed cell" is means a cell into which (or into an ancestor of which) has been introduced, by means of recombinant nucleic acid techniques, a nucleic acid molecule, i.e., a sequence of codons formed of nucleic acids (e.g., DNA or RNA) encoding a protein of interest. The introduced nucleic acid sequence may be present as an extrachromosomal or chromosomal element.

By "DNA of interest" is meant any DNA sequence which encodes a protein or other molecule which is desirable for delivery (particularly intravenous or gastrointestinal delivery, more particularly intravenous delivery) to a mammalian subject by transformation of an intestinal cell, preferably an intestinal epithelial cell. The sequence is generally operatively linked to other sequences which are needed for its expression such as a promoter. The phase "DNA of interest" is not meant to be limited to DNA, but includes any nucleic acid (e.g., RNA or DNA) that encodes a protein or other molecule desirable for administration.

By "protein" is meant a polypeptide (native (i.e., naturally-occurring) or mutant), oligopeptide, peptide, or other amino acid sequence. As used herein, "protein" is not limited to native or full-length proteins, but is meant to encompass protein fragments having a desired activity or other desirable biological characteristic, as well as mutants or derivatives of such proteins or protein fragments that retain a desired activity or other biological characteristic. Mutant proteins encompass proteins having an amino acid sequence that is altered relative to the native protein from which it is derived, where the alterations can include amino acid substitutions (conservative or non-conservative), deletions, or additions (e.g., as in a fusion protein). "Protein" and "polypeptide" are used interchangeably herein without intending to limit the scope of either term.

By "promoter" is meant a minimal DNA sequence sufficient to direct transcription. "Promoter" is also meant to encompass those promoter elements sufficient for promoter-dependent gene expression controllable for cell-type specific, tissue-specific or inducible by external signals or agents; such elements may be located in the 5' or 3' regions of the native gene.

By "intestinal cell specific promoter" is meant a promoter which directs expression of an operably linked DNA sequence when bound by transcriptional activator proteins, or other regulations or transcription, which are unique to an intestinal cell (e.g., an intestinal epithelial cell, or a specific type of intestinal epithelial cell (e.g., small intestine cell, large intestine cell, glandular cell, or absorptive cell)). For example, by "intestinal cell specific promoter" is meant a intestinal cell specific promoter that directs expression in an intestinal epithelial cell, such as promoters of sucrase, lactase-phlorizin hydrolase, and carbonic anhydrase. Exemplary intestinal cell promoters are described in Boll et al. 1991 *Am. J. Hum. Genet.* 48: 889–902; Brady et al. 1991 *Biochem. J.* 277: 903–5Drummond et al. 1996 *Eur. J. Biochem.* 236: 670–81; Olsen et al. 1994 *FEBS Lett.* 342: 325–8; Rodolosse et al. 1996 *Biochem. J.* 315: 301–6; Sowden at al. 1993 *Differentiation* 53: 67–74; Traber 1990 *Biochem. Biophys. Res. Commun.* 173: 765–73; Trabe et al. 1992 *Mol. Cell. Biol.* 12: 3614–27; Troelsen at al. 1994 *FEBS Lett.* 342: 291–6; Troelsen et al. 1994 *FEBS Lett.* 342: 297–301; and Troelsen et al. 1992 *J. Biol. Chem.* 267: 20407–11.

By "operably linked" is meant that a DNA coding sequence and a regulatory sequence(s) are connected in such a way as to permit gene expression of the coding sequence when the appropriate molecules (e.g., transcriptional activator proteins) are bound to the regulatory sequence(s).

By "operatively inserted" is meant that the DNA of interest introduced into the cell is positioned adjacent a DNA sequence which directs transcription and translation of the introduced DNA (i.e., facilitates the production of, e.g., a polypeptide encoded by a DNA of interest) and is thus positioned so that the coding sequence is expressed.

By "mammalian subject" or "mammalian patient" is meant any mammal for which gene therapy is desired, including human, porcine, bovine, equine, canine, and feline subjects.

By "substantially free" (e.g., as used in the phase "substantially free of lipofectin, dendrimer, or viral particles" (especially viral particles capable of introducing a nucleic acid sequence into a host cell)) is meant containing relatively little or substantially none of the recited compound or agent, e.g., the formulation contains relatively little or substantially none of the recited compound or agent, e.g., the recited compound or agent is present at less than 5% of the total composition, preferably less then 1%, more preferably less than 0.1%, most preferably less than 0.01% to 0.001% to undetectable or contaminating levels.

Overview of the Invention

The present invention features compositions and methods for delivery of a gene product by genetic alteration of an intestinal cell, preferably an intestinal epithelial cell of a mammalian patient. The gastrointestinal (GI) tract is a hollow tube that forms a continuous path through the body. Cells that separate it from the true interior of the body line its interior space, or "lumen." The lumen of the GI tract is actually "outside" the body, and is separated from it by a single continuous layer of cells (FIG. 1). Anything that passes into the GI tract through the mouth remains in the exterior space, and cannot enter the body proper and its bloodstream unless it first crosses the cells that line the GI tract.

The method of therapeutic gene product delivery of the invention focuses on the cells that line the lumen of the GI tract. By delivery of the transforming formulation comprising the DNA of interest into the GI tract (e.g., via the mouth), the therapeutic DNA of interest does not enter the bloodstream of the patient. The formulation comprising the DNA of interest, given externally, is absorbed into cells lining the lumen of the GI tract. The DNA is then expressed within these cells.

Preferably, the transformed intestinal cells express a protein encoded by the DNA of interest and secrete a therapeutically effective amount of the protein into the bloodstream or into the gastrointestinal tract, preferably into the bloodstream via natural secretory pathways. Once in the circulation, therapeutic proteins that serve as replacement protein therapy act in the same manner as if they were naturally expressed by the subject. Alternatively or in addition, where the therapeutic gene product is an exogenous protein that provides a desired therapeutic effect (e.g., antibiotic activity), the drug exhibits the same activity as if it were delivered by conventional injection methods. The ultimate therapeutic effects are the same, but avoids the major limitations of proteins as pharmaceuticals. Thus, the invention can serve as a platform to administer recombinant DNA by mouth of cells of the intestinal tract (i.e., the enteric route), allowing for delivery of a wide variety of protein pharmaceuticals, systemically as well as locally, thus making the invention well suited to a broad spectrum of therapeutic applications.

Preferably, the intestinal cell into which the DNA of interest is introduced and expressed is an epithelial cell of the intestine, and may be an intestinal cell of either the small or large intestine. By genetic alteration of intestinal epithelial cells, the method of the invention can provide short-term expression of the DNA of interest. Although most approaches to gene-based therapy require, and seek long term expression of the therapeutic gene, the present invention employs short-term expression, which provides a variety of important advantages. First, short-term expression allows for adjustment of the does of the therapeutic gene according to the subject's needs. This capability is a consequence of the fact that the cells that line the intestine are normally lost within about two or three days (FIG. 2). When treatment is intended to be short-term, or when it is no longer desired, the administered DNA is rapidly purged from the body along with the intestinal cells that contain it. Moreover, because the target cells are short lived and terminally differentiated, there is reduced risk of long-term complications from DNA integration (i.e., mutagenesis).

Preferably, the DNA of interest encodes either insulin, a growth hormone, clotting factor VIII, intrinsic factor, erythropoietin, Factor IX, and all other blood factors that may be lacking, e.g., plasma proteins, hormones or plasma protease inhibitors. Where the target for protein delivery is the gastrointestinal tract, the DNA of interest can encode phenylalanine transporter (for phenylketonuria), lactase for lactase deficiency, intrinsic factor, or other brush border enzymes and transporters. Preferably, the DNA of interest is operably linked to a promoter capable of expressing the gene of interest at adequate levels. Promoters include both ubiquitously functioning promoters such as the viral CMV and RSV promoters or intestinal cell type specific promoters such as the sucrase or lactase promoters (Traber et al. *Molec. Cell. Biol.,* 1992, 12(8): 3614–27).

The invention will now be described in further detail.

Vectors and Constructs

Any nucleic acid vector having a eukaryotic promoter operably linked to a DNA of interest can be used in the invention to transform an intestinal cell. The vectors containing the DNA sequence (or the corresponding RNA sequence) which may be used in accordance with the invention may be any eukaryotic expression vector containing the DNA or the RNA sequence of interest. For example, a plasmid can be cleaved to provide linear DNA having ligatable termini. These termini are bound to exogenous DNA having complementary, like ligatable termini to provide a biologically functional recombinant DNA molecule having an intact replicon and a desired phenotypic property.

Techniques for production of nucleic acid constructs for expression of exogenous DNA or RNA sequences in a host are known in the art (see, for example, Kormal et al. *Proc. Natl. Acad. Sci.* USA, 84: 2150–2154, 1987; Sambrook et al. *Molecular Cloning: A Laboratory Manual,* 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

Various vectors (e.g., bacterial vectors, or vectors capable of replication in eukaryotic and prokaryotic hosts) can be used in accordance with the present invention. Preferably the vector is capable of replication in both eukaryotic and prokaryotic hosts. Numerous vectors which can replicate in eukaryotic and prokaryotic hosts are known in the art and are commercially available. In general, such vectors used in accordance with the invention are composed of a bacterial origin of replication and a eukaryotic promoter operably linked to a DNA of interest.

Preferably, the DNA construct contains a promoter to facilitate expression of the DNA of interest within an intestinal epithelial cell. Preferably the promoter is a strong, eukaryotic promoter. Exemplary eukaryotic promoters for facilitating transcription in a eukaryotic cell include promoters from cytomegalovirus (CMV), mouse mammary tumor virus (MMTV), Rous sarcoma virus (RSV), and adenovirus. More specifically, exemplary promoters include the promoter from the immediate early gene of human CMV (Boshart et al., *Cell* 41: 521–530, 1985) and the promoter from the long terminal repeat (LTR) of RSV (Gorman et al., *Proc. Natl. Acad. Sci.* USA 79: 6777–6781, 1982). Of these two promoters, the CMV promoter is preferred as it provides for higher levels of expression than the RSV promoter.

For eukaryotic expression (e.g., in an intestinal epithelial cell), the construct preferably comprises at least a eukaryotic promoter operably linked to a DNA of interest, which is in turn operably linked to a polyadenylation sequence. The polyadenylation signal sequence may be selected from any of a variety of polyadenylation signal sequences known in the art. Preferably, the polyadenylation signal sequence is the SV40 late polyadenylation signal sequence. The construct may also include sequences in addition to promoters which enhance expression in intestinal epithelial cells (e.g., enhancer sequences, introns). For example, the construct can include one or more introns, which can increase levels of expression of the DNA of interest, particularly where the DNA of interest is a cDNA (e.g., contains no introns of the naturally-occurring sequence). Any of a variety of introns known in the art may be used. Preferably, the intron is the human β-globin intron and inserted in the construct at a position of 5' to the DNA of interest.

Other components such as a marker (e.g., an antibiotic resistance gene (such as an ampicillin resistance gene) or β-galactosidase) to aid in selection of cells containing and/or expressing the construct (e.g., during the process of vector construction), an origin of replication for stable replication of the construct in a bacterial cell (preferably, a high copy number origin of replication), a nuclear localization signal, or other elements which facilitate production of the DNA construct, the protein encoded thereby, or both. A schematic of an exemplary construct useful in the method of the invention is shown FIG. 3.

Therapeutic Gene Products and Conditions Amendable to Treatment by Intestinal Cell Gene Therapy The DNA of interest can be any DNA sequence encoding any protein or other gene product for which intravenous therapy and/or therapy for the gastrointestinal tract is desirable. For example, intravenous protein therapy is appropriate in treating a mammalian subject having an inherited or acquired disease associated with a specific protein deficiency (e.g., diabetes, hemophilia, anemia, severe combined immunodeficiency). Such protein deficient states are amenable to treatment by replacement therapy, i.e., expression of a protein to restore the bloodstream levels of the protein to at least normal levels. Secretion of a therapeutic protein into the gastrointestinal tract (e.g. by secretion of the protein into the mucosal secretion) is appropriate where, for example, the subject suffers from a protein deficiency associated with absorption of nutrients (e.g. deficiency in instrinsic factor, sucrase, lactase, digestive enzymes, or transporters).

Alternatively, the mammalian subject may have a condition which is amenable to treatment by expression or overexpression of a protein which is either normally present in a healthy mammalian subject or is foreign to the mammalian subject. For example, intravenous protein therapy can be used in treatment of a mammalian subject having a viral (e.g., human immunodeficiency virus (HIV), Epstein-Barr virus (EBV), or herpes simplex virus (HSV)), bacterial, fungal, and/or parasitic infection, particularly where the infection is chronic, i.e., persisting over a relatively long period of time. The intestinal cell gene therapy of the invention may also be used to enhance expression of a protein present in a normal mammal, or to express a protein not normally present in a normal mammal, in order to achieve a desired effect (e.g., to enhance a normal metabolic process). For example, cells of the intestinal tract of a dairy cow may be transformed with DNA encoding bovine growth hormone (BGH) in order to enhance levels of BGH in the bloodstream and enhance milk production.

Alternatively, the DNA of interest can be a DNA encoding a gene product that can repair a defect in the intestinal cell targeted for genetic alteration. For example, the DNA can encode gene products associated with lipoprotein production by intestinal cells.

The DNA of interest is preferably obtained from a source of the same species as the mammalian subject to be treated (e.g. human to human), but this is not an absolute requirement. DNA obtained from a species different from the mammalian subject can also be used, particularly where the amino acid sequences of the proteins are highly conserved and the xenogeneic protein is not highly immunogenic so as to elicit a significant, undesirable antibody response against the protein in the mammalian host. Further, the DNA can be synthetically produced via chemical synthesis and/or via genetic engineering in cells.

Exemplary, preferred DNAs of interest include recombinant or isolated DNA sequences encoding insulin, growth hormone, clotting factor VIII, intrinsic factor, and erythropoietin. Of particular interest is intravenous protein therapy of a mammalian subject (e.g., a bovine, canine, feline, equine, or human subject, preferably a bovine or human subject, more preferably a human subject) by expression of DNA encoding a protein (e.g., insulin, growth hormone, clotting factor VIII, or erythropoietin) in a transformed mammalian intestinal cell. Preferably, the subject is a human subject and the DNA expressed encodes a human protein (e.g., human insulin, human growth hormone, human cloning factor VIII, or human erythropoietin). Other exemplary DNAs of interest include tissue plasminogen activator (tPA), urokinase, streptokinase, acidic fibroblast growth factor, basic fibroblast growth factor, tumor necrosis factor alpha, tumor necrosis factor β, transforming growth factor β, platelet-derived growth factor, endothelian, and soluble CD4. In general, the DNAs of interest can be a sequence encoding a gene that decreases production of a gene product (e.g., genes involved in lipoprotein production by intestines) or can be nucleic acids that do not encode genes (e.g., ribozymes or antisense nucleic acids) but that are useful for decreasing lipoprotein production by the intestines. The DNAs of interest can also be synthetic nucleic acids, e.g., modified synthetic bases that can alter sensitivity of the DNA of interest to endogenous nucleases or increase cellular uptake. The DNAs of interest can encode a gene product for immunotherapy, which can facilitate development of immunity to infection, or development of tolerance to treat autoimmune disease, as in type I diabetes mellitus or rheumatoid arthritis. Table 1 provides a list of exemplary proteins and protein classes which can be delivered by the intestinal cell gene therapy of the invention.

TABLE 1

Exemplary Proteins and Protein Classes for Use in the Invention

SPECIFIC EXEMPLARY PROTEINS

| | |
|---|---|
| insulin | interferon-α2B |
| human growth hormone (hGH) | transforming growth factor (TGF) |
| erythropoietin (EPO) | ciliary neurite transforming factor (CNTF) |
| clotting factor VIII | insulin-like growth factor-1 (IGF-1) |
| bovine growth hormone (BGH) | granulocyte macrophage colony stimulating factor |
| platelet derived growth factor (PDGF) | interferon-α2A |
| clotting factor VIII | brain-derived neurite factor (BDNF) |
| thrombopoietin (TPO) | insulintropin |
| IL-1 | tissue plasminogen activator (tPA) |
| IL-2 | urokinase |
| IL-1 RA | streptokinase |
| superoxide dismutase (SOD) | adenosine deamidase |
| catalase | calcitonin |
| fibroblast growth factor (acidic or basic) | arginase |
| neurite growth factor (NGF) | phenylalanine ammonia lyase |
| granulocyte colony stimulating factor (G-CSF) | γ-interferon |
| L-asparaginase | pepsin |
| uricase | trypsin |
| chymotrypsin | elastase |
| carboxypeptidsse | lactase |
| sucrase | intrinsic factor |
| calcitonin | parathyroid hormone(PTH)-like hormone |
| Ob gene product | cholecystokinin (CCK) |
| glucagon | insulinotrophic hormone |
| glucagon-like-peptide I (GLP-1) | |

TABLE 1-continued

Exemplary Proteins and Protein Classes for Use in the Invention

EXEMPLARY CLASSES OF PROTEINS

| | |
|---|---|
| proteases | pituitary hormones |
| protease inhibitors | growth factors |
| cytokines | somatomedians |
| chemokines | immunoglobulins |
| gonadotrophins | interleukins |
| chemotactins | interferons |
| lipid-binding proteins | |

Various disease conditions are amenable to treatment using the intestinal cell gene therapy of the invention. One skilled in the art can recognize the appropriate protein that should be produced by the invention for treating specific disease conditions. Exemplary diseases that are amenable to treatment using the subject invention, and exemplary, appropriate proteins which can be used in treating these diseases, are shown in Table 2.

TABLE 2

Exemplary Disease Conditions Amenable to Treatment Using the Invention

| | |
|---|---|
| Enzyme Deficiency | Endotoxic Shock/Sepsis |
| Adenosine deaminase[1] | Lipid-binding protein (LBP) |
| Purine nucleotide phosphorylase | Anemia |
| Galactosidase | Erythropoietin |
| β-glucuronidase | Growth Factors (for use in wound healing, induction of red blood cell formation, etc.) |
| Antioxidants for Cancer Therapy | |
| Superoxide dismutase | |
| Catalase | |
| Cancer | |
| α-Interferon | Epidermal growth factor |
| factor | G-CSF |
| γ-Interferon | γ-Interferon |
| α-IL1 | Transforming growth |
| Phenylalanine ammonia lyase | Erythropoietin |
| factor-1 | Thrombopoietin |
| Arginase | Insulin-like growth |
| L-asparaginase | Insulin |
| Uricase | Human growth hormone |
| Granulocyte colony stimulating factor (G-CSF) | Diabetes |
| Monoclonal antibodies | Insulin |
| Tissue necrosis factor | Glucagon |
| Cardiovascular | Insulinotrophic hormone |
| Disease | Clotting disorders |
| Tissue plasminogen activator | Clotting factor VIII |
| Urokiase (native or chimeric) | Gastrointestinal and |
| α₁-antitrypsin | Pancreatic Deficiencies |
| Antithrombin-III | Pepsin (for esophageal |
| Other proteases | reflux) |
| or protease inhibitors | Trypsin |
| Apolipoproteins (particularly B-48) | Chymotrypsin |
| Circulating Scavenger Receptor | Elastase |
| APO A1[2] | Carboxypeptidase |
| Obesity and Feeding | Lactase (for lactose |
| Ob gene product | deficiency) |
| Cholecystokinin (CCK) | Sucrase |
| Bone diseases | Intrinsic Factor |
| Calcitonin | (pernicious anemia) |
| PTH-like hormone | |

Organ-Specific Autoimmune diseases (target of antibody in parentheses)

Myasthenia gravis (acetylcholine receptors)
Graves' disease (thyroid-stimulating hormone receptor)
Thyroiditis (thyroid, peroxidase)
Insulin-resistant diabetes with acanthosis nigricans or with ataxia telangiectasia (Insulin receptor)
Allergic rhinitis, asthma (Beta₂-adrenergic receptors)
Juvenile insulin-dependent diabetes (insulin, GAD65)
Pernicious anemia (gastric parietal cells, vitamin $B_{12}$ binding site of

TABLE 2-continued

Exemplary Disease Conditions Amenable to Treatment Using the Invention intrinsic factor)
Addison's disease (adrenal cells)
Idiopathic hypoparathyroidism (parathyroid cells)
Spontaneous infertility (sperm)
Premature ovarian failure (interstitial cells, corpus luteum cells)
Pemphigus (intercellular substance of skin and mucosa)
Bullous pemphigoid (basement membrane zone of skin and mucosa)
Primary biliary cirrhosis (mitochondria)
Autoimmune hemolytic anemia (erythrocytes)
Idiopathic thrombocytopenic purpura (platelet)
Idiopathic neutropenia (neutrophils)
Vitiligo (melanocytes)
Osteosclerosis and Meniere's disease (type II collagen)
Chronic active hepatitis (nuclei of hepatocytes)
Systemic Autoimmune Diseases (defect/organ affected in parentheses)

Goodpasture's syndrome (basement membranes)
Rheumatoid arthritis (γ-globulin, EBV-related antigens, collagen types II and III)
Sjögren's syndrome (γ-globulin, SS-A (Ro), SS-B (La))
Systemic lupus erythematosus (nuclei, double-stranded DNA, single-stranded DNA, Sm ribonucleoprotein, lymphocytes, erythrocytes, neurons, γ-globulin)
Scleroderm (nuclei, Scl-70, SS-A(Ro), SS-B (LA), centromere)
Polymyositis (nuclei, Jo-1, PL-7, histadyl-tRNA synthetase, threonyl-tRNA synthetase, PM-1, Mi-2)
Rheumatic fever (myocardium heart valves, choroid plexus)

[1]For treatment of severe combined immunodeficiency
[2]Converts low-density lipoproteins to high-density lipoproteins Numerous proteins that are desirable for intravenous protein therapy are well known in the art and the DNA encoding these proteins has been isolated. For example, the sequence of the DNAs encoding insulin, human growth hormone, intrinsic factor, clotting factor VIII, and erythropoietin are available from GenBank and/or have been described in the scientific literature (e.g., human clotting factor VIII gene: Gitschier et al., Nature 312:326–330, 1984; Wood et al., Nature 312:330–317, 1984; human intrinsic factor: Herwit et al., Genomics 10:432–440, 1991). Proteins commonly used in treatments can be used in the gene therapy procedures of the present invention. Such proteins are disclosed in, for example, the Physicians' Desk Reference (1994 Physicians' Desk Reference (1994 Physicians' Desk Reference, 48th Ed., Medical Economics Data Production Co., Montvale, N.J.; incorporated by reference) and can be dosed using methods in Harrison's Principles of Internal Medicine and/or the AMA "Drug Evaluations Annual" 1993, all incorporated by reference.

Where the DNA encoding a protein of interest has not been isolated, this can be accomplished by various, standard protocols well known to those of skill in the art (see, for example, Sambrook et al., ibid; Suggs et al., Proc. Natl. Acad. Sci. USA 78:6613–6617, 1981; U.S. Pat. No. 4,394, 443; each of which are incorporated herein by reference with respect to identification and isolation of DNA encoding a protein of interest). For example, genomic or cDNA clones encoding a specific portion can be isolated from genomic or cDNA libraries using hybridization probes designed on the basis of the nucleotide or amino acid sequences for the desired gene. The probes can be constructed by chemical synthesis or by polymerase chain reaction (PCR) using primers based upon sequence data to amplify DNA fragments from pools or libraries (U.S. Pat. Nos. 4,683,195 and 4,683,202). Nucleotide substitutions, deletions, additions, and the like can also be incorporated into the polynucleotides, so long as the ability of the polynucleotide to hybridize is not substantially disrupted (Sambrook et al.

ibid). The clones can be expressed or the DNA of interest can be excised or synthesized for use in outer constructs. If desired, the DNA of interest can be sequenced using methods well known in the art.

In a preferred embodiment, the construct used in the present invention is designed so as to enhance protein secretion from the transformed intestinal epithelial cell into the bloodstream. Intestinal epithelial cells are normally polarized, with the apical surface oriented toward the lumen of the gastrointestinal tract and the basolateral surface oriented toward the blood supply.

The intestinal epithelium is the major absorptive surface in animals, and as such transports substances preferentially from the intestinal lumen into blood. Although these processes have been most widely studied for hexoses, amino acids and electrolytes, it has become increasingly clear that larger molecules are absorbed as well. For example, small polypeptides are absorbed into absorptive cells, and in newborn animals antigencity is achieved as the result of the absorption of material antibody proteins. There is also a variety of evidence that various digestive enzymes from the pancreas, as well as other large molecules such as insulin and albumin, cross the intestinal epithelium at substantial rates (see references). Indeed, the whole plasma albumin pool leaks across the intestinal epithelium every day.

Permeability to proteins has been seen primarily in the duodenum and terminal ileum, but proteins are also known to be absorbed from the lower portions of the large bowel, and suppositories have been used for this purpose therapeutically. For discussions of the intestinal absorption of protein, see, e.g., Liebow et al 1975 *Science* 189:472–474; Goetze et al. 1975 *Nature* 257:607–609; Goetze et al. 1976 *Lancet* ii:494–495; Goetze et al. 1978 *Biochim. Biophys. Acta* 512:214–220; Heinrich et al 1979 *Klin Wochenscht* 57:1295–1297; Lake-Bakaar et al. 1980 *Gut* 21:580–586; Martin et al. 1957 *Nature* 199:815–817; Avakian et al. 1964 *Clin. Pharmacol. Ther.* 5:712–715; Megel et al. 1964 *Arch. Biochem. Biophys.* 108:193–199; Alpers et al. 1967 *J. Biol. Chem.* 242:5617–5622; Katayama et al. 1972 *Biochim. Biophys. Acta* 288:172–180; Katayama et al. 1972 *Biochim. Biophys. Acta* 288:181–189; Urban et al. 1982 *J. Pediatr. Gastroenterol. Nutr.* 1:267–272; Katayama et al. 1968 *Biochim. Biophys. Acta* 167: 613-; Moriya et al. 1967 *Chem. Phar. Bull.* 15:1662–1668; Ambrus et al. 1967 *Clin. Pharmacol. Ther.* 8:362–368; Alpers et al. 1970 *M. Gastroenterology* 58:833–842; Brambel, F. W. R. 1958 *Biol. Rev.* 33:488-; Lev et al. 1973 *Gastroenterologia* 65:60-; Waller et al. 1972 *Nature* 177:608; Danforth et al. 1959 *Endocrinology* 65:118; and Warshaw et al. 1974 *Gastroenterologia* 66:987. Proteins that are manufactured in the gut and targeted for secretion into the blood include hormones such as CCK (choleocystokinin), secretin, gut glucagon, vasoacitve intestinal peptide (VIP), gastric inhibitory peptide (GIP), somatostatin, neuropeptide Y (NPY), islet amyloid polypeptide (IAPP), polypeptide Y (PPY), glucagon-like peptide I (GLPI), as well as a variety of lipoproteins important in lipid metabolism.

The DNA of interest preferably contains a secretion signal which either directs secretion of the protein primarily into the gastrointestinal tract or directs secretion of the protein primarily into the bloodstream. Secretion signals can be identified by, for example, site-directed mutagenesis of DNA encoding a blood stream-targeted protein (e.g., insulin) or a intestinal lumen-targeted protein (e.g., protease various digestive enzymes, and mucin). The mutants can be screened by expression of the mutated DNA in intestinal cells and subsequently determining the ratio of, for example, lumenal to intravenous expression. Alternatively, intravenous-directed secretion signals and intestinal lumen-directed secretion signals can also be identified by constructing recombinant, chimeric proteins composed of, for example, a putative intravenous secretion signal inserted into an intestinal lumen-directed protein. Intravenous secretion signals would then be identified by their ability to re-direct expression of the lumen-directed protein into the bloodstream. Putative intravenous secretion signals and intestinal lumen secretion signals can also be identified by comparison of DNA and amino acid sequences of proteins which are preferentially secreted into either the bloodstream or the gastrointestinal tract, respectively. Areas of homology or common motifs among the proteins could then be tested as described above.

The DNA of interest may be inserted into a construct so that the therapeutic protein is expressed as a fusion protein (e.g., a fusion protein having β-galactosidase or a protein thereof at the N-terminus and the therapeutic protein at the C-terminal portion). Production of a fusion protein can facilitate identification of transformed cells expressing the protein (e.g., by enzyme-linked immunosorbent assay (ELISA) using an antibody which binds to the fusion protein).

It may also be desirable to produce altered forms of the therapeutic proteins that are, for example, protease resistant or have enhanced activity relative to the wild-type protein. For example, where an enzyme is to be secreted into the gastrointestinal tract, it may be advantageous to modify the protein so that it is resistant to digestive proteases. Where a protein to be secreted requires processing that is not available in intestinal cells, the protein may be modified to allow correct processing. For example, proinsulin can be modified to allow processing to mature insulin in intestinal cells. Further, where the therapeutic protein is a hormone, it may be desirable to alter the protein's ability to form dimers or multimeric complexes. For example, insulin modified so as to prevent its dimerization has a more rapid onset of action relative to wild-type, dimerized insulin.

The construct containing the DNA of interest can also be designed so as to provide for site-specific integration into the genome of the target intestinal cell. For example, a construct can be produced such that the DNA of interest and the promoter to which it is operably linked are flanked by the position-specific integration markers of *Saccharomyces cerevisiae* Ty3. The construct for site-specific integration additionally contains DNA encoding a position-specific endonuclease which recognizes the integration markers. Such constructs take advantage of the homology between the Ty3 retrotransposon and various animal retroviruses. The Ty3 retrotransposon facilitates insertion of the DNA of interest into the 5' flanking region of many different tRNA genes, thus providing for more efficient integration of the DNA of interest without adverse effect upon the recombinant cell produced. Methods and compositions for preparation of such site-specific constructs are described in U.S. Pat. No. 5,292,662, incorporated herein by reference with respect to the construction and use of such site-specific insertion vectors.

Intravenous and gastrointestinal protein therapy by transformation of intestinal cells Intestinal epithelial cells transformed according to the invention facilitate expression of a DNA of interest, and can be expressed at high levels, particularly where the DNA of interest is operably linked to a strong eukaryotic promoter (e.g., CMV, MMTV promoters). The expressed protein is then secreted into the bloodstream or into the gastrointestinal tract. The protein so expressed and secreted is thus useful in treating in mammalian subject having a variety of conditions. For example, secretion of an appropriate protein into the gastrointestinal tract is useful in preventing or controlling various diseases, e.g., in treating chronic infections of the small and/or large intestine (e.g., bacterial or fungal infections); in treating degenerative disorders of intestinal epithelium; in treating intestinal malabsorption syndromes (e.g., sprue); or as a replacement or supplemental protein therapy.

In a preferred embodiment, the proteins are secreted into the bloodstream at levels sufficient for intravenous protein therapy. Bloodstream levels of the therapeutic protein may be enhanced by integration of multiple copies of the DNA of interest into the genome of the target cells, and/or by operably linking a strong promoter (e.g., a promoter from CMV) and/or enhancer elements to the DNA of interest in the construct. Bloodstream levels may also be enhanced by transformation of a greater number of target cells in the subject. As discussed above, secretion of the therapeutic protein may also be enhanced by incorporating leader sequences, amino acid sequences motifs, or other elements which mediate intravenous-directed secretion into the sequence of the therapeutic protein.

Where the present invention involves the transformation of absorptive epithelial cells of the small intestine and/or columnar epithelial cells of the large intestine, the method of intestinal in vivo gene therapy provides the additional advantage that expression of the gene product by the mammalian subject is short-term due to the relatively rapid turnover rate of these short-lived epithelial cells (e.g., the average life of a short-lived epithelial cell is from about 2 to 4 days, and can be from about 2 to 3 days). "Short-term" as used herein means that the desired gene product is delivered to the gastrointestinal tract or bloodstream over a few to several days (e.g., as short as 12 hours to 36 hours; or for a period up to 2 days, 3 days, or 4 days, generally no more than 4 days). In contrast "long-term" as used herein in the context of the present invention means that cells having longer life in the intestine (i.e., cells that are not turned over so quickly, e.g. stem cells) express the desired gene product for several weeks to months. Thus, the type of cell transformed (e.g., absorptive cell or stem cell) at least in part determines the period of protein delivery (e.g., short term or long term, respectively).

Short-term gene product expression in the mammalian subject allows for tight regulation of the amount of therapeutic gene product delivered to the host. Further, because the gene therapy method of the invention generally involves non-invasive methods of administration of the transforming nucleic acid, the desired therapy can be easily achieved by repeated administration. The administration of the vector to the gut can provide both short and long term effects. If mature absorptive cells are targeted, the the effect is short term (2–4 days); alternatively, if the vectors is targeted to the stem cells at the base of the villi, then long term effects should occur. Thus the method of the invention can be used to achieve both short and long term effects.

The nature of the intestinal cell transformation achieved using the in vivo gene therapy methods of the invention can be either transient or stable. By "transient transformation" is meant that the introduced nucleic acid for the remaining life of the mature cell and/or the introduced nucleic acid is not passed on to daughter cells following cell division. In contrast, "stable transformation" means that the nucleic acid is replicated and passed on to the daughter cells after cell division. Transient transformation is particularly advantageous where the physician desires a short period of therapy, administration of only a small amount of therapeutic gene product, and/or the ability to titrate dose by repeated administration. In general, the nature of the transformation can also, at least in part, determine the period of delivery of the desired gene product, i.e., whether gene product delivery is short term (e.g., a few hours to few days with transient transformation) or long-term (e.g., several weeks or months with stable transformation).

The actual number of transformed intestinal epithelial cells required to achieve therapeutic levels of the protein of interest will vary according to several factors including the nature of the intestinal cell transformation achieved (e.g., either transient or stable transformation), the protein to be expressed, the level of expression of the protein by the transformed cells, the rate of protein secretion, the partitioning of the therapeutic protein between the gastrointestinal tract and the blood stream, and the condition to be treated. For example, the desired intravenous level of therapeutic protein can be readily calculated by determining the level of the protein present in normal subject (for treatment of a protein deficiency), or by determining the level of protein required to effect the desired therapeutic result (e.g., using information about effective therapeutic amounts of proteins for which therapy is already established, e.g., insulin, hGH, etc.). The level of expression of the protein from transformed cells and the rate of protein secretion can be readily determined in an animal model in vivo (e.g., in a rodent model, e.g., rat or mouse). Given the levels of protein expression and secretion in the animal model, and the estimated intravenous level of therapeutic protein desired, the number of cells which should be transformed to effect the desired levels can be readily calculated, and the gene therapy protocol carried out accordingly.

Formulations

The nucleic acid for in vivo transformation of intestinal cells can be formulated in a variety of ways in order to facilitate delivery to the surface of the intestinal cells. The form (e.g., liquid, solid, pill, capsule) and composition of the formulation will vary according to the method of administration used. For example, where the formulation is administered orally, the nucleic acid can be formulated as a tablet, pill, capsule, solution (e.g., gel, syrup, slurry, or suspension), or other suitable form. Where the nucleic acid is delivered by direct placement in the intestinal tract, the nucleic acid can be formulated as a suppository (e.g., for rectal administration) or as a solution administered via endoscopic catheterization.

The formulation can also vary with the intestinal site targeted. For example, the nuclease activity associated with the small bowel is greater than that associated with the large bowel. Thus, formulations for transformation of small bowel cells and/or formulations administered orally which must pass through the small bowel before reaching the desired target cell may contain anti-nuclease compositions to prevent degradation of the administered nucleic acid. Methods for preparation of various types of formulations, and administration of such formulations, are well known in the art (see, e.g., Remington's Pharmaceutical Sciences, Maack Publishing Co., Easton, Pa.).

The formulation can contain components in addition to nucleic acid, where the additional components aid in the delivery of the nucleic acid to the target intestinal cell. The DNA of interest can be present in a pharmaceutical composition of the invention with additional components such as, but not limited to, stabilizing compounds and/or biocompatible pharmaceutical carriers, e.g., saline, buffered saline, dextrose, or water. The DNA of interest can also be administered alone or in combination with other agents, including other therapeutic agents (e.g., drugs, or hormones). The formulation can also contain organic and inorganic compounds to, for example, facilitate DNA delivery to and uptake by the target cell (e.g., detergents, salts, chelating agents, etc.).

Where the formulation is administered orally, the formulation can contain buffering agents or comprise a coating to protect the nucleic acid from stomach acidity and/or facility swallowing. In addition or alternatively, the oral formulation can be administered during an interdigestive period (between meals or at bedtime) when stomach pH is less acidic or with the administration of inhibitors of HCL secretion such as H2 blockers (e.g., cimetidine) or proton pump inhibitors (e.g., PROLISEC™) The formulation can also comprise a time-release capsule designed to release the nucleic acid upon reaching the surface of the target intestinal cells. For example, time-release formulations can be designed to deliver the nucleic acid at a particular location within the intestine, (e.g., to deliver the nucleic acid for transformation of cells of the small intestine (nucleic acid release shortly after entry into the intestine)) or for transformation of cells at a lower position in the intestinal tract (e.g., cells of the large intestine). The formulation can also be designed to allow for slow release in a particular area (e.g., in the absence of rush peristalis). The formulation can also comprise nuclease inhibitors to enhance the amount of intact nucleic acid available for transformation of the target intestinal cells.

The DNA of interest can be formulated as a DNA- or RNA-liposome complex formulation. Such complexes comprise a mixture of lipids which bind to genetic material (DNA or RNA), providing a hydrophobic core and hydrophilic coat which allows the genetic material to be delivered into cells. Liposomes that can be used in accordance with the invention include DOPE (dioleyl phosphatidyl ethanol amine), CUDMEDA (N-(5-cholestrum-3-β-ol 3-urethanyl)-N',N'-dimethylethylene diamine). Of particular interest is the use of the cationic transport reagents and polyfunctional cationic cytofectins described in U.S. Pat. No. 5,527,928 and PCT published application nos. WO 96/10555 and WO 97/11935, incorporated herein by reference for the manufacturer and use of such agents. When the DNA of interest is introduced using a liposome, it is preferable to first determine in an animal model (e.g., in a mammalian animal model, preferably rat or mouse) the optimal values for the DNA:lipid ratios and the absolute concentrations of DNA and lipid as a function of cell death and transformation efficiency for the particular type of cell to be transformed. These values can then be used in or extrapolated for use in other subjects (e.g., human subjects).

Other formulations can also be used in accordance with the present invention. Such formulations include DNA or RNA coupled to a carrier molecule (e.g., an antibody or a receptor ligand) which facilitates delivery to host cells for the purpose of altering the biological properties of the host cells. By the term "chemical modification" is meant modifications of nucleic acids to allow, for example, coupling of the nucleic acid compounds to a carrier molecule such as a protein or lipid, or derivative thereof. Exemplary protein carrier molecules include antibodies specific to the cells of a targeted intestinal cell or receptor ligands, i.e., molecules capable of interacting with receptors associated with a cell of a targeted intestinal cell.

In one embodiment, the formulation is primarily composed of naked DNA (e.g., DNA that is not contained within a viral vector) and/or is substantially free of detergent (e.g., ionic and nonionic detergents, e.g., polybrene, etc.) or mucolytic agents (e.g., N-acetylcysteine, dithiothreitol, and pepsin). Further, the formulation for transformation of intestinal cells according to the invention can be substantially free of poliferation enhancing factors (e.g., factors that enhance uptake of nucleic acid into cells that do not divide rapidly) such as epidermal growth factor, angiogenesis factor, insulin-like growth factor-1, insulin-like growth factor-2, transforming growth factor-α, gastrin, methotrexate, fluorouracil, floxuridine, and arabinoside-C. Preferably, the formulation is prepared to target epithelial cells of the intestine, more preferably absorptive cells of the small intestine and/or columnar epithelial cells of the large intestine. Intestinal stem cells are not a preferred target for transformation according to the present invention, particularly where short-term therapy is desired.

Administration and in vivo transformation of intestinal cells

Gastrointestinal administration of the DNA of interest can be accomplished by a variety of methods well known in the art. In general, the methods useful in connection with the present invention involve the exposure of the targeted cells of the intestine (e.g., intestinal epithelial cells, specifically epithelial cells of the small or large intestine) to a formulation comprising nucleic acid encoding a therapeutic gene product of interest. Such methods include, but are not limited to, oral administration and direct administration of the nucleic acid to the lumen of the intestine through use of, for example, a suppository, endoscope, or catheter. Preferably, the nucleic acid is administered to the subject orally.

The amount of DNA to transform a sufficient number of the targeted intestinal cells and provide for expression of therapeutic levels of the protein can be readily determined based upon such factors as the efficiency of in vivo transformation in animal models, the levels of protein expression achieved in the in vivo animal model, and the susceptibility of the targeted intestinal cells to transformation. For example, where the targeted intestinal cell is a small intestine epithelial cell and the nucleic acid is administered orally as naked DNA, the naked DNA is administered at a concentration sufficient to reach the small intestine to provide a DNA concentration effective transform the targeted small intestine epithelial cells and provide for therapeutic levels of the protein in either the blood or the gastrointestinal tract. In general, the nucleic acid is administered ranging from about 1 mg to 1 gram, generally about 100 mg to about 1 gram, depending on the formulation used. In general, dosages for humans are approximately 200 times dosages effective in a rat or mouse model. For example, to date the most effective dose in an animal model (rat) is from about 32 μg to about 64 μg. Thus, The expected effective dosage in humans is from about 6 mg to about 12 mg. The formulation can be administered, for example, several times daily, daily, or several times a week, depending upon the desired level of protein expression desired and/or the period over which therapy is desired.

Assessment of protein therapy

The delivery system of the present invention can be used in connection with any therapeutic gene product, particularly proteins, that are desired for administration. While the delivery system can be used with proteins whose efficacy in intravenous therapies has not yet been tested, the delivery system can also be used with DNAs encoding proteins or other gene products of well-established efficacy (e.g., hGH, insulin, etc.). Furthermore, given the examples below, the ordinarily skilled artisan can readily determine that, since the delivery system efficiently provides insulin and hGH in the bloodstream in an animal model after delivery of the DNA of interest, then delivery of other proteins can also be readily achieved using the claimed delivery system.

Since the delivery system of the claimed invention can be used in connection with a wide variety of therapeutic gene products, the effects of expression of the gene products encoded by the DNA of interest can be monitored in a variety of ways. Generally, a sample of blood or a sample of intestinal mucosal secretions from the subject can be assayed for the presence of the therapeutic protein. Appropriate assays for detecting a protein of interest in such samples are well known in the art. For example, where intestinal cell gene therapy has been performed to accomplish intravenous protein therapy, a sample of blood can be tested for the presence of the protein using an antibody which specifically binds the therapeutic protein in an ELISA assay. The assay can be performed either qualitatively or quantitatively. The ELISA assay, as well as other immunological assays for detecting the protein in a sample, are described in *Antibodies: A Laboratory Manual* (1988, Harlow and Lane, ed.s Cold Spring Harbor Laboratory, Cold Spring Harbor, N.Y.).

Alternatively, or in addition, the efficacy of the protein therapy can be assessed by testing a sample of blood or intestinal secretion for an activity associated with the therapeutic protein (e.g., an enzymatic activity). For example, where the therapeutic protein has antimicrobial activity, the efficacy of therapy can be tested by examining the ability of the test sample to inhibit bacterial growth. Furthermore, the efficacy of intestinal cell gene therapy can be assessed by monitoring the condition of the mammalian subject for improvement. For example, where the therapeutic protein is erythropoieton, the subject's blood is examined for iron content or other parameters associated with anemia. Where the therapeutic protein is insulin, the efficacy of the therapy can be assessed by examining blood glucose levels of the mammalian subject or by measuring insulin (e.g., by using the human insulin radioimmunoassay kit, Linco Research Inc., St. Louis, Mo.).

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is average molecular weight, temperature is in degrees Centigrade, and pressure is at or near atmospheric.

Example 1

Figure 4:
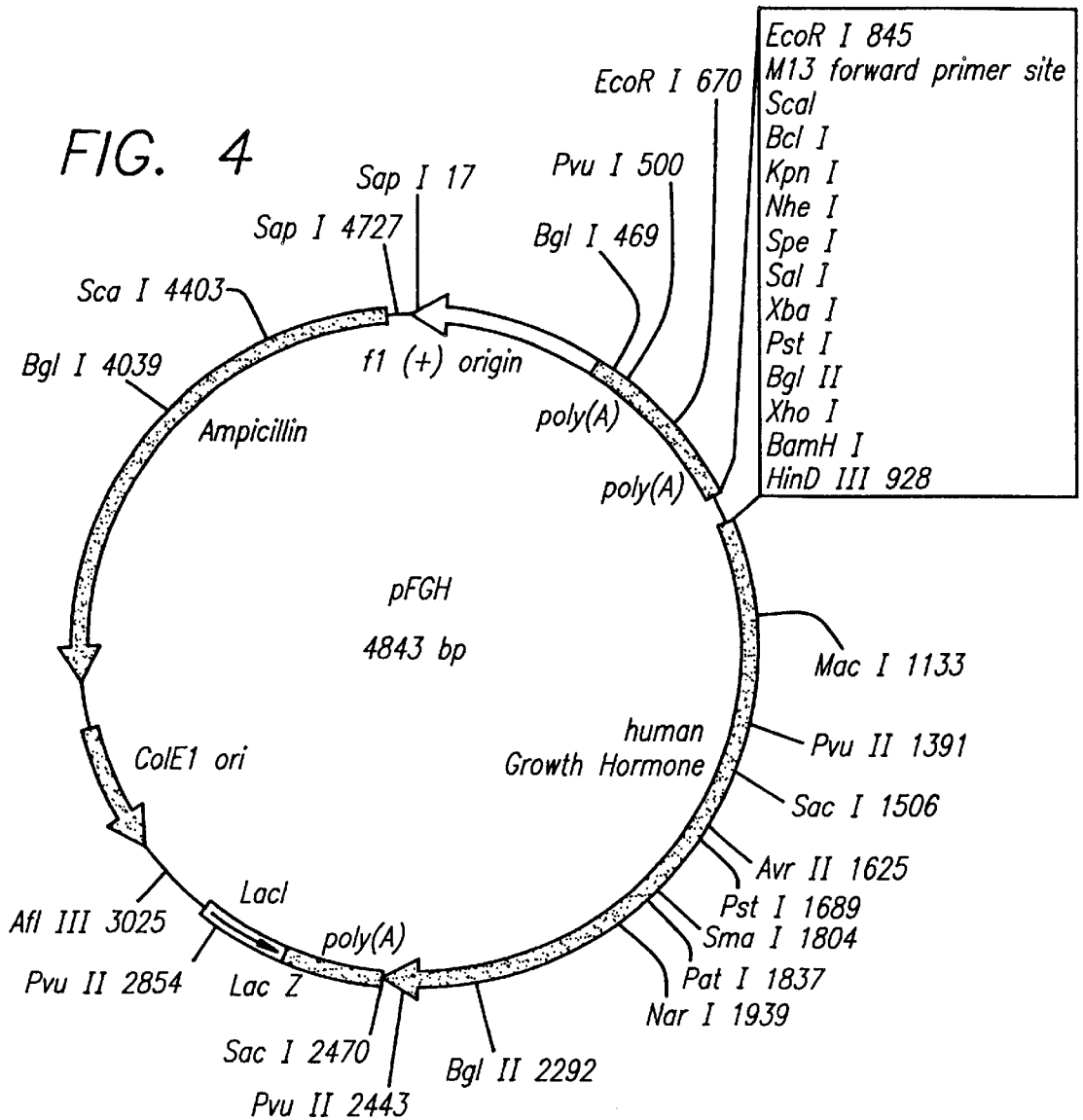
FIG. 4 is a map of the pFGH construct, which contains the human growth hormone genomic sequence.

Construction of vectors expressing human growth hormone (hGH) for intestinal cell transformation Four constructs for expression of human growth hormone (hGH) were prepared using techniques well known in the art (see, for example, Sambrook et al. ibid). The first construct, pFGH, contains the genomic hGH DNA sequence inserted in the commercially available vecotr pBLUESCRIPT SK+™ (Stratagene, La Jolla, Calif.) (FIG. 2). Because the hGH coding sequence is not linked to a promoter, this vector provides for no or only low-level hGH expression. Thus, the pFHG construct serves as a negative control for hGH expression in the intestine. The second construct, pFGH.CMV, was constructed by operably inserting the promoter from the immediate early gene of human CMV upstream of the genomic hGH sequence of the pFGH vector (FIG. 3). The third construct, pFGH.chymo, was constructed by operably inserting the rat chymotrypsin B gene promoter upstream of the genomic hGH sequence of the pFGH vector (FIG. 4). The fourth construct, pFGH.RSV, was constructed by operably inserting the promoter from the long terminal repeat (LTR) of RSV upstream of the genomic hGH sequence of the pFGH vector.

Example 2

In vivo gene transfer of DNA encoding human growth hormone by introduction of naked DNA into the intestinal lumen pFGH.CMV was used to transform intestinal epithelium of approximately 300 g adults rats (pFGH.CMV 10 rats; pFGH.CMV with lipofectin, 4 rats; pFGH.CMV with polycationic dendrimers, 4 rats; negative control (PBS), 1 rat; and negative control (no surgery), 8 rats.

The rats were anesthetized with pentobarbital. A laparotomy was performed and the upper duodenum or terminal ileum identified. A 5 cm length of intestine was ligated, a small aliquot of venous blood was obtained, and 400 µl of phosphate-buffered saline (PBS) containing pFGH.CMV, or 400 µl of PBS alone (negative control no. 1), were slowly injected or infused into the intestine and left in place for 15 min. The amount of solution used produces a slight expansion of the bowel. The vector-containing solutions were composed of 20–200 µg DNA per 400 µl in PBS; 32 µg DNA per 400 µl in PBS with 6% lipofectin (a cationic lipid used to increase transformation efficiency); or 32 µg DNA per 100 µl in PBS with 128 µg of dendrimers. The elastic ties were then removed, the bowel replaced in its normal location, and the abdomen closed with sutures. Recovery after surgery was nominal, and no sign or symptoms of disease were noticed over the next 48 hours. At autopsy, the intestine looked normal in all respects. This transfection method provides direct access of the vector to about 5–10% of the intestinal cells.

After 24 hours, the rats were again anesthetized with pentobarbital, tissue extracted, and a sample of blood taken prior to sacrifice. The blood samples from before and after transfection were prepared, growth hormone measured in each sample using an immunoassay for hGH. The levels of hGH in the serum samples were measured using the hGH radioimmune assay (Nichols Institute) except that bound samples were washed three times and placed into new tubes prior to gamma counting. Each assay was performed in triplicate and compared to a set of control samples.

Rats receiving the pFGH.CMV vector along (naked DNA) expressed higher levels of hGH in samples of systemic and portal vein blood (FIG .5), in comparison to background levels of hGH cross-reactivity in rats receiving no DNA. The addition of lipofectin did not increase transformation efficiency (as measured by the presence of hGH in the blood samples), but rather significantly decreased transformation efficiency relative to use of naked DNA. Likewise, transformation efficiency in rats receiving DNA plus dendrimers was decreased relative to use of naked DNA alone. Thus, administration of naked DNA encoding hGH in a simple PBS solution not only resulted in successful transformation of intestinal cells, but also resulted in more efficient intestinal cell transformation and subsequent hGH intravenous secretion than administration of the same construct in a formulation containing lipofectin or dendrimers. Furthermore, plasma levels were similarly elevated after both duodenal and ileal administration, indicating that intestinal cell transformation was achieved at similar levels of efficiency at these two sites.

Example 3

Figure 6:
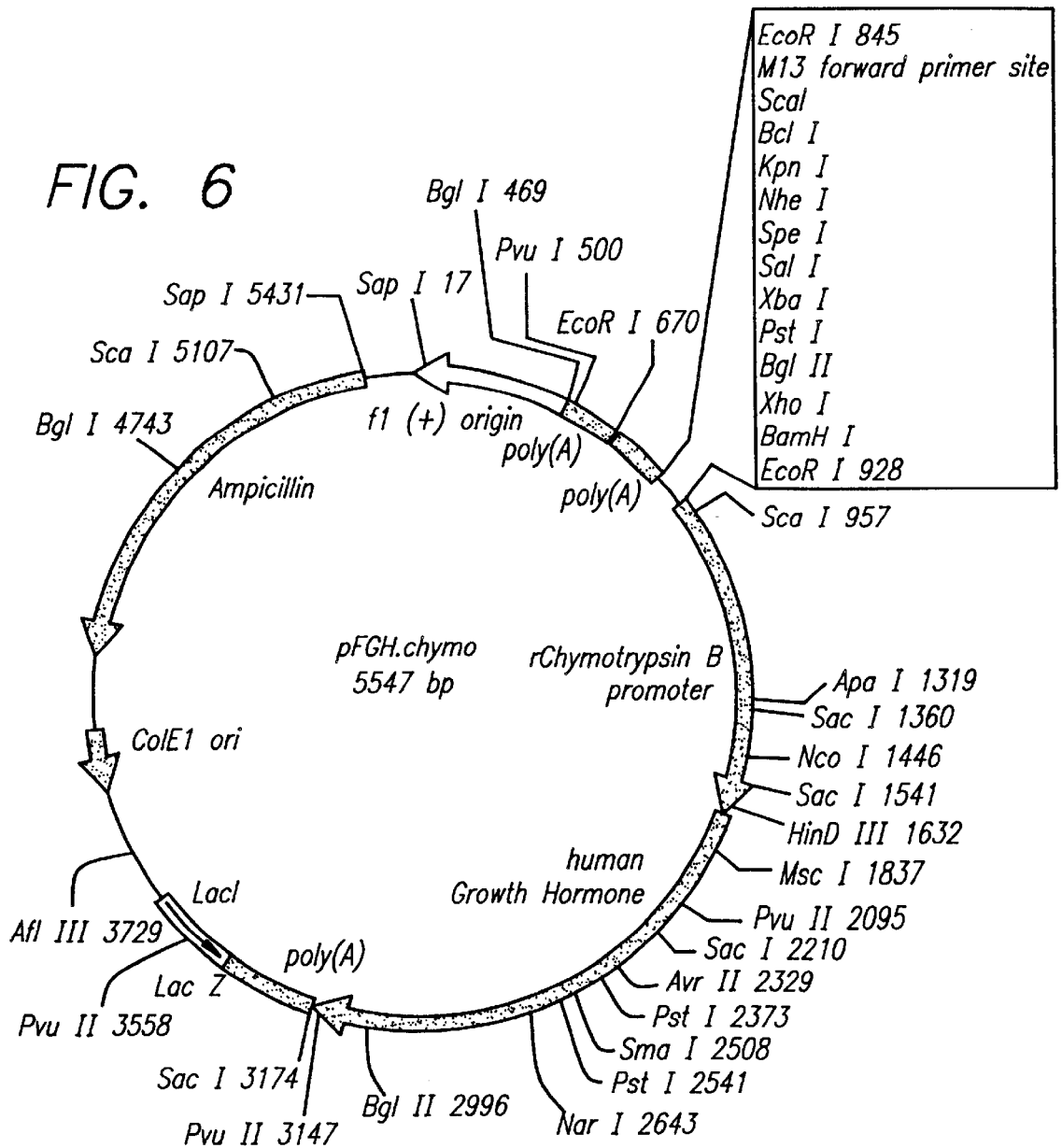
FIG. 6 is a map of the pFGH.chymo construct, which contains the human growth hormone genomic sequence operably linked to the chymotrypsin B promoter.

Construction of vectors expressing human insulin (hIns) for intestinal cell transformation Two constructs for expression of human insulin and a human insulin mutant were prepared using techniques well known in the art (see, for example, Sambrook et al., Ibid). The first construct, pBAT14.hins, contains a cDNA sequence encoding human insulin which is inserted in the commercially available vecotr pBLUESCRIPT SK+™ (Stratagene, La Jolla, Calif.) (FIG. 6A). The human insulin encoding sequence is operably lined to a promoter from the immediate early gene of human CMV, which is positioned upstream of the first intron of human β-globin and of the human insulin-encoding cDNA sequence. The second construct, pBAT16.hInsG1.M2, was constructed by operably linking the CMV promoter upstream of a nucleotide sequence encoding a mutant of human insulin (FIG. 6B). The mutation in the human insulin mutant changes the second protease site between peptides C and A into a furin recognition site in order to allow proper processing in non-endocrine cells.

Example 4

In vivo gene transfer of DNA encoding human insulin by introduction of naked DNA into the intestinal lumen Experimental diabetes was induced in rats by intravenous injection of 50 mg/kg of streptozotocin. Streptozotocin treatment produces high blood sugar levels within 24 hours after injection. Immediately after streptozotocin injection, the rat was anesthetized with pentobarbital and a laparotomy performed as described above. One ml of material (either PBS alone, PBS with the insulin vector pBAT16.hInsG1.M2 was instilled into the duodenum just below the pyloric junction in both streptozotocin treated and control animals. The material was primarily composed of naked DNA; no lipofectin, dendrimers, or other material to enhance introduction of the DNA into the cells was used. The abdomen was then closed with sutures. Control dye measurements showed that over a period of about an hour the material remains in great part in the upper portion of the duodenum. Recovery after surgery was nominal, and no signs or symptons of disease were observed over the next 48 hours. At autopsy, the intestine looked normal in all respects.

Figure 7:
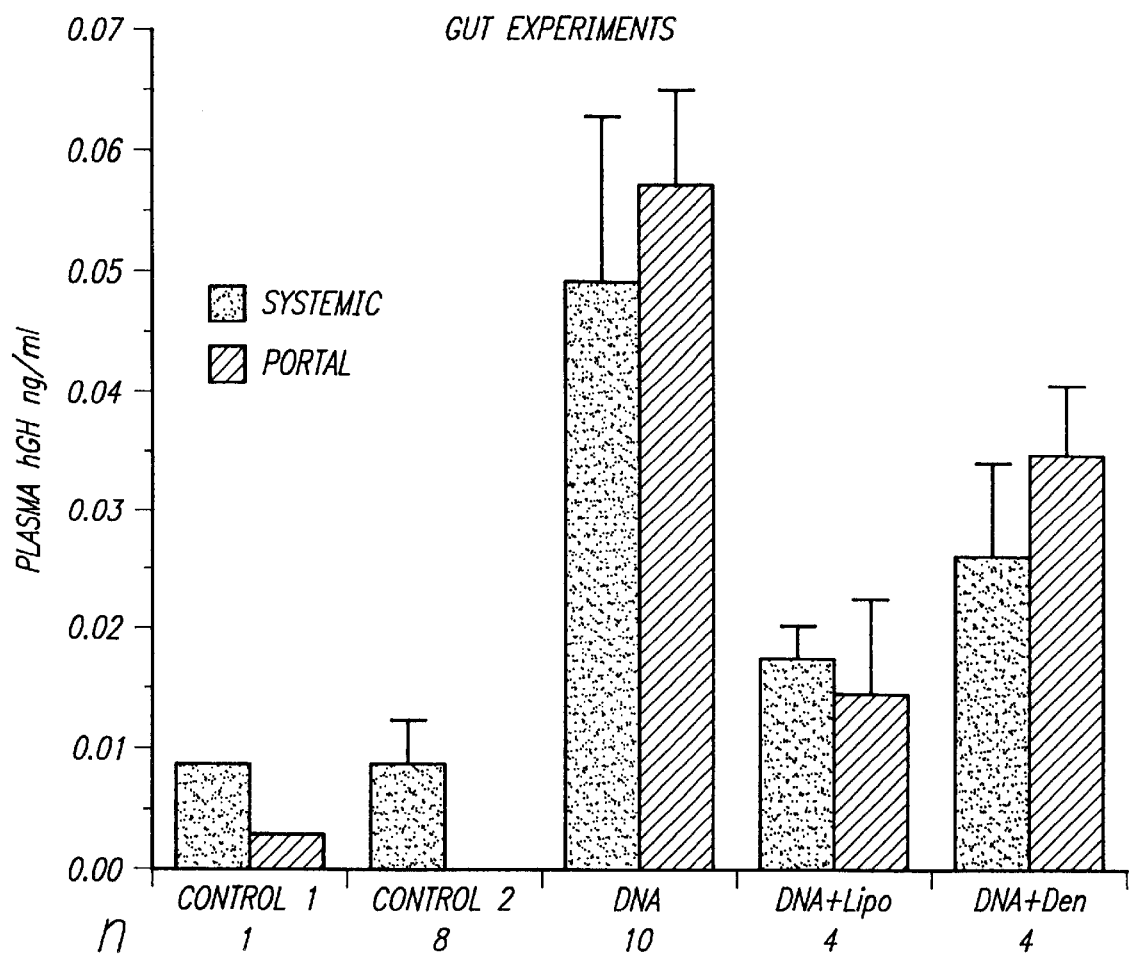
FIG. 7 is a graph showing the levels of human growth hormone in systemic blood (filled bars) and portal vein blood (hatched bars) after exposure of intestinal segments to a solution composed of DNA encoding human growth hormone.

Blood samples were obtained immediately prior to surgery and every 24 hours after treatment. The rats that received no treatment (no surgery or streptozotocin treatment) were used as negative controls to show the normal blood glucose level in untreated rats. Results are shown in FIG. 7. Streptozotocin-induced diabetes was ameliorated in the insulin vector-treated rats for about 48 hours after treatment and blood glucose was maintained at normal or near normal levels. These data show that the intestinal cells of the rats were successfully transformed with the human insulin-encoding vector, human insulin was both expressed and secreted into the blood stream, and that human insulin successfully suppressed the diabetic syndrome in the streptozotocin-treated rats. Furthermore, when the vector was not longer effective (after about 48 hours), diabetes re-emerged in the streptozotocin-treated rats.

Example 5

Figure 5:
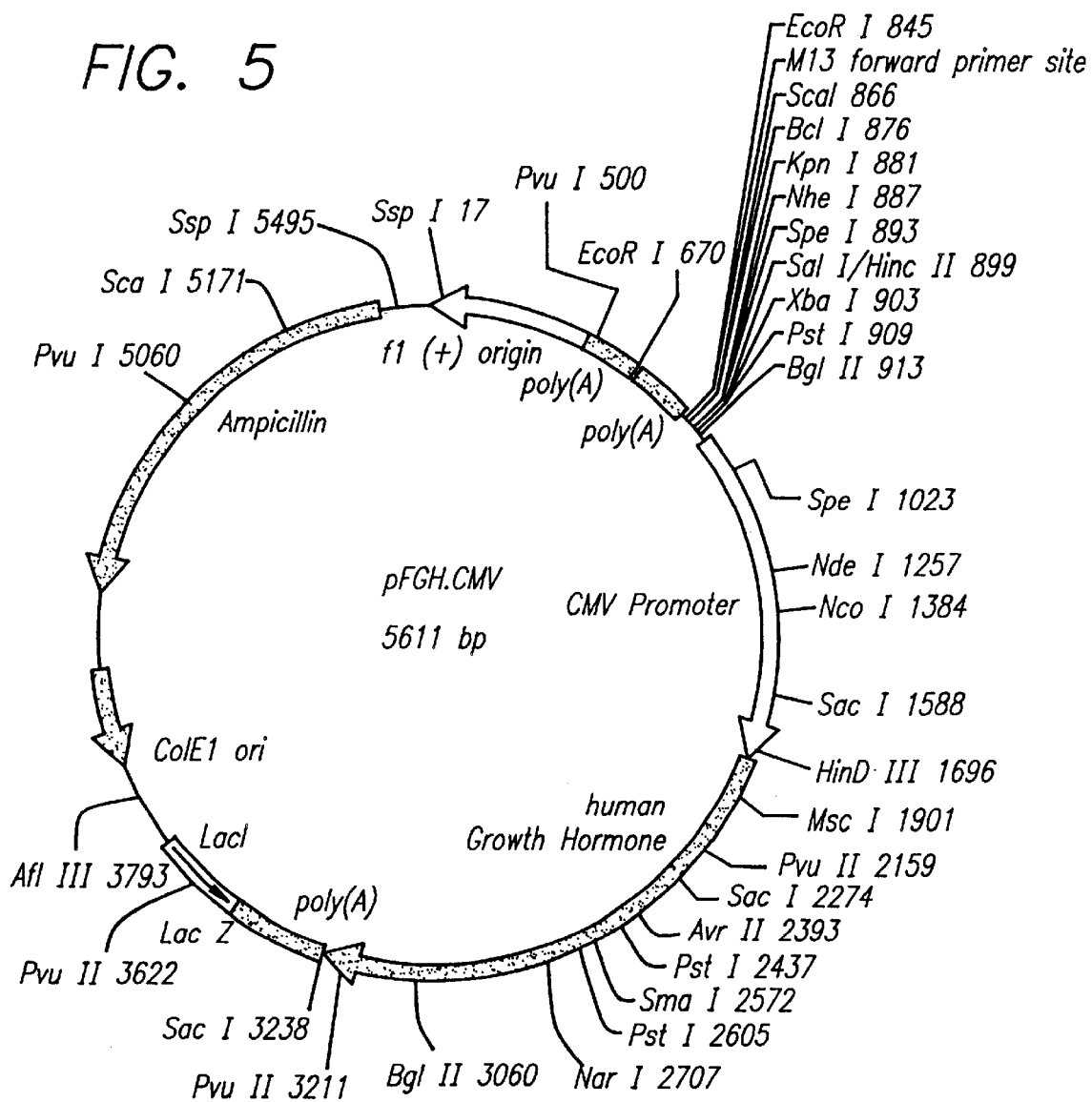
FIG. 5 is a map of the pFGH.CMV construct, which contains the human growth hormone genomic sequence operably linked to the CMV promoter.

In vivo gene transfer of DNA encoding human growth hormone (hGH) with repeated delivery of naked DNA into the intestinal lumen The pFGH construct (FIG. 4) and the pFGH.CMV construct (FIG. 5) were prepared for administration to test animals. The construct pGFP.CMV.N2.CMV, which is identical to pFGH.CMV except that the coding region of the plasmid encode green fluorescent protein (GFP; Clontech, Calif.) rather than hGH, served as a control.

Male Sprague-Dawley rats, 260–280 g, were fed a balanced meal of lab chow at all times except when fasted overnight prior to surgery (water ad lib). Animals were anesthetized with pentobarbital (50 mg/kb body weight) and an indwelling polyethylene catheter placed into the duodenum. The catheter was inserted through the proximal body wall, below the diagram, and tracked subcutaneously over the rib cage to a point just behind and between the ears. here the catheter was passed through the skin and was immobilized with three ligatures. The external end of the catheter was capped with an air tight, removable plug.

Animals were rested for two days prior to first administration of DNA. On day zero each animal received 32 μg DNA in 1.6 ml phosphate buffered saline (PBS), injected into the catheter. Thirty-two micrograms of either the pFGH.CMV or pFOXGFP.N2.CMV (control) was injected daily into the indwelling catheter of awake rats, to simulate oral dosing. Control animals received an equal amount of the control plasmid.

In order to assess delivery of hGH into the bloodstream, blood was drawn by heart puncture in late morning, and plasma prepared by sedimentation at 12,000×g for 15 minutes. The supernatants were stored at −80° C. prior to being assayed for hGH. hGH was measured by immunoassay employing a human specific, coated bead method (Nichols Institutes, San Juan Capistrano, Calif.).

Figure 11:
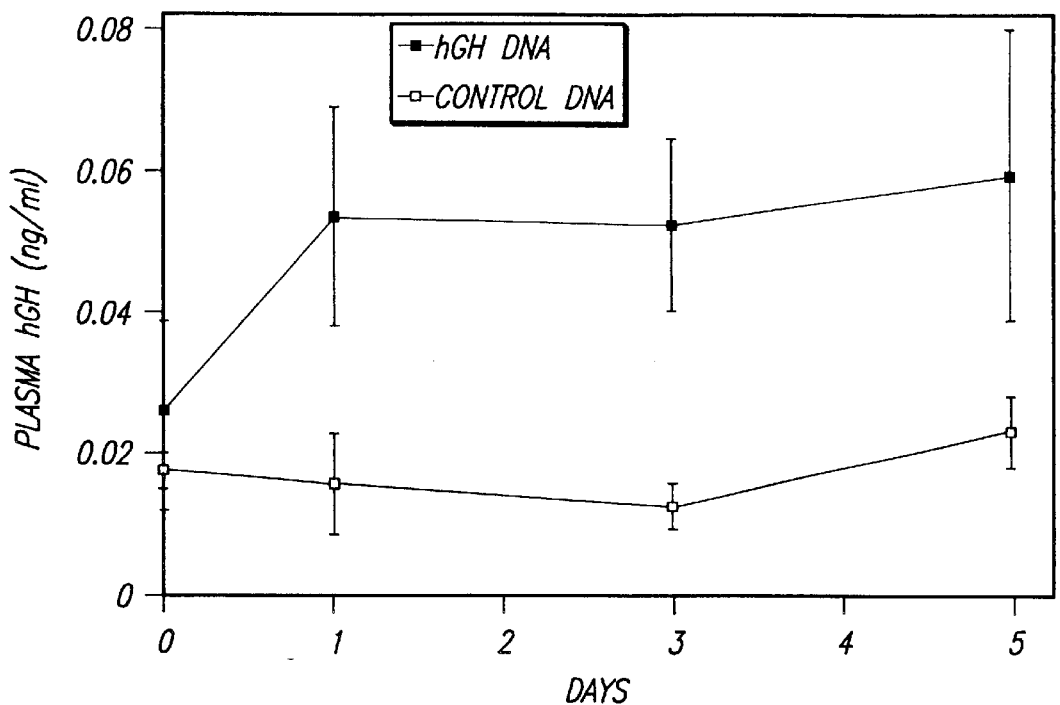
FIG. 11 is a graph showing plasma levels of human growth hormone (hGH) after administration of DNA encoding hGH (closed square) or control DNA (open squares) via an indwelling duodenal catheter in awake animals. Each data point represents the average of three experiments.
Figure 12:
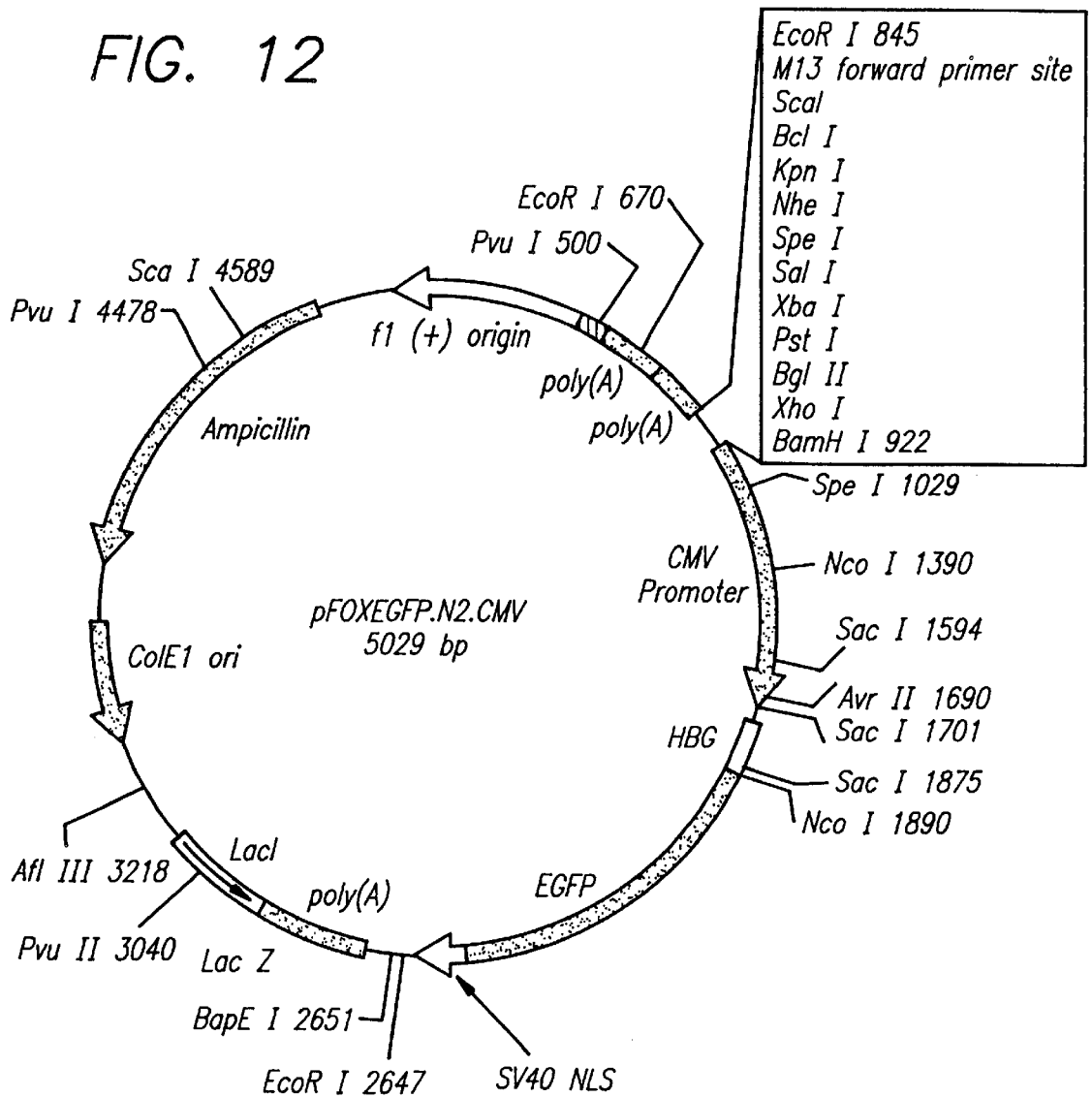
FIG. 12 is a map of the pFOXEGFP.N2.CMV construct, which encodes green fluorescent protein under control of a CMV promoter.

FIG. 11 shows the effect of repeated dosing of hGH-encoding DNA. Plasma levels of hGH rose well above background after 24 hours, and remained elevated for the duration of the study. These data demonstrate that, using the gene-based protein delivery system of the invention, protein delivery can be maintained over time by repeated dosing.

Example 6

Figure 8:
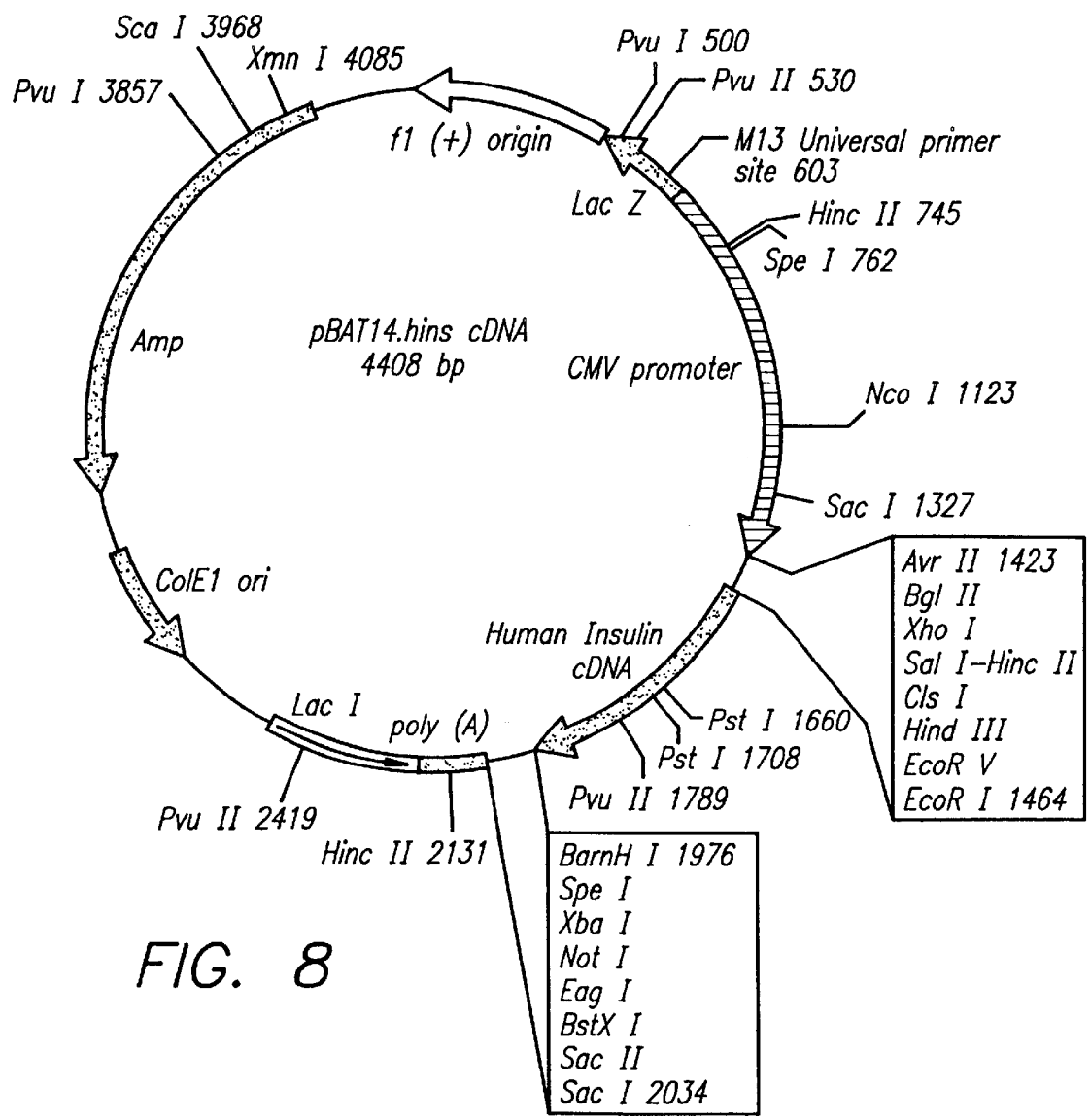
FIGS. 8 and 9 are maps of the pBAT14.hIns and pBAT16.hInsG1.M2 constructs, which contain a nucleotide sequence encoding human insulin or a mutant of human insulin, respectively, operably linked to a CMV promoter.
Figure 9:
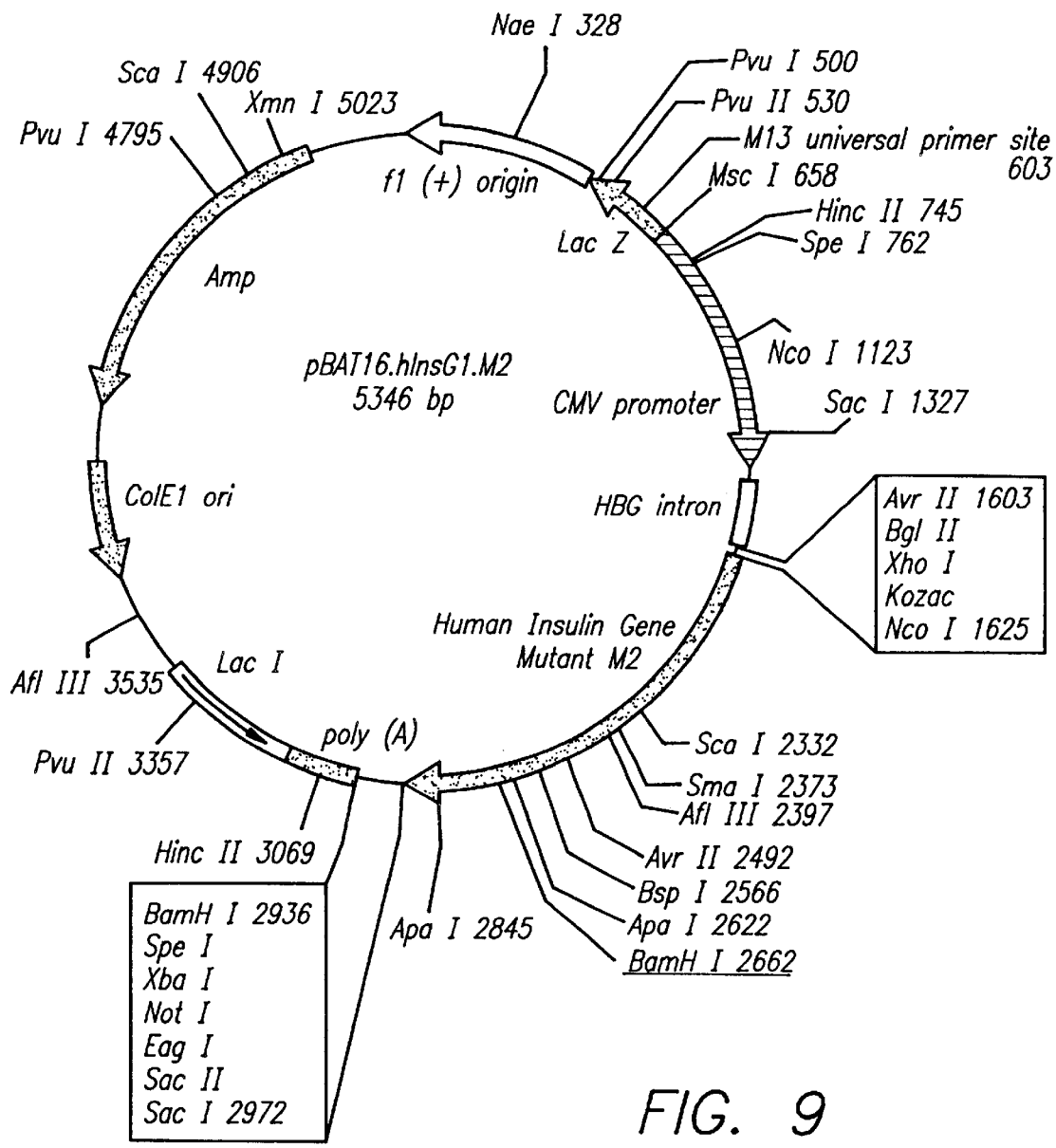
Figure 10:
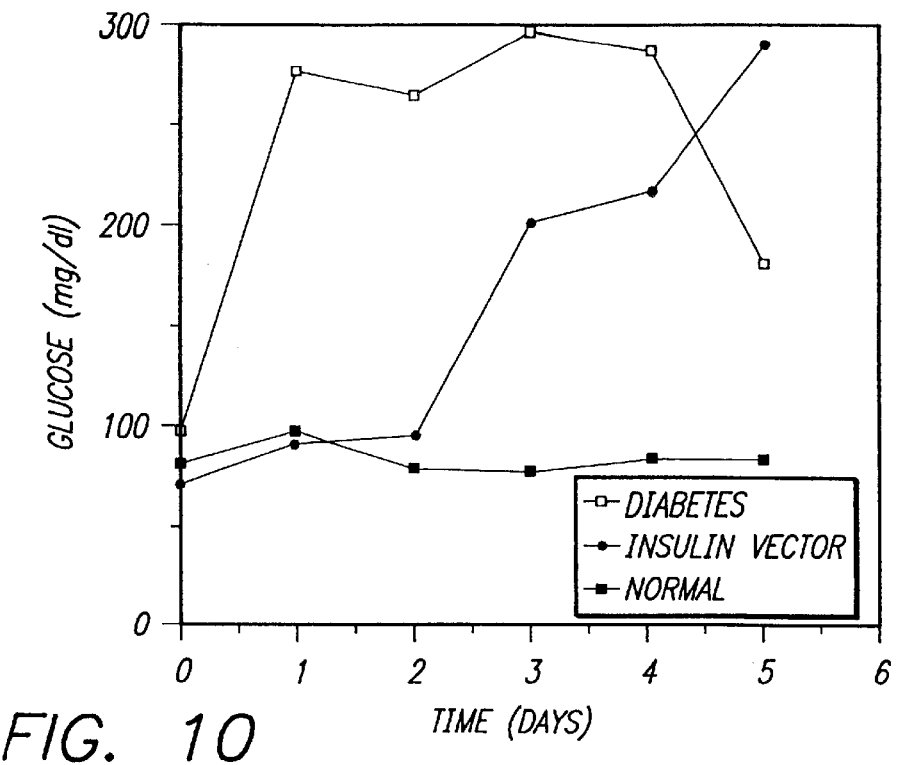
FIG. 10 is a graph showing amelioration of diabetes by intestinal cell transformation according to the invention. Open squares, blood glucose levels (mg/dl) in normal rats; open squares with center dot, blood glucose levels in rats having streptozotocin-induced diabetes; closed squares, blood glucose levels in rats having streptozotocin-induced diabetes and treated by intestinal cell transformation with an insulin-encoding vector.

Identification and characterization of transformed intestinal epithelial cells following administration of naked DNA The intestinal cell types transformed using the method of the invention, and expression of a protein encoded by the transforming construct is determined by examining expression of green fluorescent protein (GFP) in rat intestinal cells after in vivo administration of a construct encoding GFP. One ml of either PBS alone (negative control) or PBS with the GFP-encoding vector pFOXEGRP.N2.CMV (FIG. 8; see also German and Wang 1994 Mol. Cell. Biol. 14:4067) is instilled into the duodenum just below the pyloric junction in rats as described in Example 4. The abdomen is then closed with sutures. At 24 hours after treatment, tissue samples are obtained from the intestine of rats and fixed in 1.5% glutaraldehyde, and frozen sections prepared. Expression of GFP is detected in the sections using a fluorescent microscope and the number and types of cells expressing GFP are determined.

Example 7

Oral gene therapy in humans using naked DNA

The DNA of interest is formulated as a capsule ("gene pill") according to methods well known in the art. The capsule comprises approximately 100 mg to 1000 mg of the DNA of interest. The capsule can additionally contain liposomes, viral uptake elements, DNAase inhibitors, and/or various enteric coatings. Preferably, the capsule is primarily composed of naked DNA (i.e., DNA without viral uptake elements, dendrimers, lipofectin, or other compounds or agents that are used in conventional formulations to enhance cellular uptake) and can additionally contain components that provide for protection of the DNA against DNAses or degradation of damage that may occur while traveling the gastrointestinal tract to reach the desired intestinal cells.

The pill is administered to the human patient in order to achieve a sufficient level of expression of the protein encoded by the DNA within the pill. The pill can be administered, for example, several times daily, daily, or several times a week, depending upon the desired level of protein expression desired and/or the period over which therapy is desired. Therapy can be assessed by, for example, examining levels of protein present in the bloodstream of the patient (where the protein is secreted into the bloodstream) or by monitoring the patient for improvement or stabilization of his condition.

Example 8

Intestinal cell gene therapy using naked DNA in a suppository

The DNA of interest is formulated as a suppository according to methods well known in the art. The suppository comprises approximately 100 mg to 1000 mg of the DNA of interest. The suppository can additionally contain liposomes, viral uptake elements, DNAase inhibitors, and/or various enteric coatings. Preferably, the suppository is primarily composed of naked DNA (i.e., DNA without viral uptake elements, dendrimers, lipofectin, or other compounds or agents that are used in conventional formulations to enhance cellular uptake) and can additionally contain components that provide for protection of the DNA against DNAses or degradation or damage that may occur while traversing the gastrointestinal tract to reach the desired intestinal cells.

The suppository is administered to the human patient in order to achieve a sufficient level of expression of the protein encoded by the DNA within the pill. The suppository can be administered, for example, several times daily, daily, or several times a week, depending upon the desired level of protein expression desired and/or the period over which therapy is desired. Therapy can be assessed by, for example, examining levels of protein present in the bloodstream of the patient (where the protein is secreted into the bloodstream), or by monitoring the patient for improvement or stabilization of his condition.

Following procedures similar to those described above, other therapeutic proteins can be expressed from DNA inserted in the genome of an intestinal epithelial cell by gene transfer according to the invention.

The invention now being fully described, it will be apparent to one of ordinary skill in the art that many changes and modifications can be made thereto without departing from the spirit or scope of the appended claims.

What is claimed is:

1. A method of delivering a secreted protein into the bloodstream of a mammalian subject, the method comprising:

introducing into the gastrointestinal tract of a mammalian subject by oral administration a construct comprising a nucleic acid molecule encoding a secreted protein and a promoter sequence operably linked to the nucleic acid molecule, wherein said construct is not packaged in a viral particle, said introducing resulting in introduction of the construct into an intestinal epithelial cell, expression of the protein in the intestinal epithelial cell and secretion of the protein from the cell and into the bloodstream of the subject.

2. The method of claim 1, wherein the intestinal epithelial cell is an absorptive cell of the small intestine.

3. The method of claim 1, wherein the intestinal epithelial cell is a columnar epithelial cell of the large intestine.

4. The method of claim 1, wherein the construct is a DNA construct formulated with a lipid.

5. The method of claim 1, wherein expression of the protein in the mammalian subject is for a period of about two to three days.

* * * * *